US008859500B2

(12) United States Patent
Salter et al.

(10) Patent No.: US 8,859,500 B2
(45) Date of Patent: Oct. 14, 2014

(54) METHOD FOR AMELIORATING PAIN BY MODIFICATION OF NMDA RECEPTORS THROUGH INHIBITION OF SRC

(75) Inventors: Michael W. Salter, Toronto (CA); Jeffrey R. Gingrich, Toronto (CA)

(73) Assignee: The Hospital For Sick Children, Toronto, Ontario (CA)

( * ) Notice: Subject to any disclaimer, the term of this patent is extended or adjusted under 35 U.S.C. 154(b) by 136 days.

(21) Appl. No.: 13/426,488

(22) Filed: Mar. 21, 2012

(65) Prior Publication Data

US 2013/0288974 A1    Oct. 31, 2013

Related U.S. Application Data

(63) Continuation of application No. 13/165,764, filed on Jun. 21, 2011, now Pat. No. 8,158,749, which is a continuation of application No. 11/512,802, filed on Aug. 29, 2006, now Pat. No. 8,003,609, which is a continuation-in-part of application No. 10/814,109, filed on Mar. 30, 2004, now Pat. No. 7,425,540.

(51) Int. Cl.
| | |
|---|---|
| A61K 38/00 | (2006.01) |
| A61K 38/17 | (2006.01) |
| C07K 14/435 | (2006.01) |
| C07K 14/005 | (2006.01) |
| C07K 7/08 | (2006.01) |
| C12N 9/12 | (2006.01) |

(52) U.S. Cl.
CPC ............ C12N 9/1205 (2013.01); C07K 14/005 (2013.01); C12N 2740/16122 (2013.01); C07K 7/08 (2013.01); A61K 38/00 (2013.01)
USPC ........... 514/17.3; 514/1.1; 514/1.2; 514/18.3; 530/300

(58) Field of Classification Search
None
See application file for complete search history.

(56) References Cited

U.S. PATENT DOCUMENTS

| | | | |
|---|---|---|---|
| 4,994,446 A | 2/1991 | Sokolovsky et al. | |
| 5,523,323 A | 6/1996 | Maccecchini | |
| 5,888,996 A | 3/1999 | Farb | |
| 5,914,403 A | 6/1999 | Nichols et al. | |
| 6,649,605 B2 | 11/2003 | Olesen et al. | |
| 6,653,354 B2 | 11/2003 | Franks et al. | |
| 6,703,489 B1 | 3/2004 | Ish-Horowicz et al. | |
| 7,425,540 B2 | 9/2008 | Salter et al. | |
| 8,003,609 B2 | 8/2011 | Salter et al. | |
| 8,158,749 B2 | 4/2012 | Salter et al. | |
| 2002/0077322 A1 | 6/2002 | Ayoub | |
| 2002/0123510 A1 | 9/2002 | Chenard et al. | |
| 2003/0050243 A1 | 3/2003 | Tymianski | |
| 2003/0224993 A1 | 12/2003 | Land et al. | |
| 2004/0082543 A1 | 4/2004 | Cheung | |
| 2005/0222042 A1 | 10/2005 | Salter et al. | |

FOREIGN PATENT DOCUMENTS

| | | |
|---|---|---|
| EP | 1244638 A2 | 10/2002 |
| WO | WO 97/46877 A1 | 12/1997 |
| WO | WO 2005/012551 A2 | 2/2005 |
| WO | WO 2005/095593 A1 | 10/2005 |
| WO | WO 2008/025130 A1 | 3/2008 |

OTHER PUBLICATIONS

Aarts et al, "Treatment of ischemic brain damage by perturbing NMDA receptor-PSD-95 protein interactions", Science, 298:846-850, (2002).
Ali et al, "NMDA receptor regulation by Src kinase signaling in excitatory synaptic transmission and plasticity", Current Opinion in Neurobiology, 11:336-342, (2001).
B. Lin et al, "Integrins regulate NMDA receptor-mediated synaptic currents", J. Neurophysiol., 89:2874-2878, (2003).
Brown et al, "Regulation, substrates and functions of src", Biochimica et Biophysica Acta, 1287:121-149, (1996).
Chen et al, "Tyrosine kinase and tyrosine phosphatase participate in regulation of interactions of NMDA receptor submit 2A with Src and Fyn mediated by PSD-95 after transient brain ischemia", Neuroscience Letters, 339:29-32, (2003).
Coyle et al, "Oxidative stress, glutamate, and neurodegenerative disorders", Science, 262:689-695 (1993).
Database Genbank CDS 4468..5511 NADH dehydrogenase subunit 2 Jul. 22, 2003, Ingman,M. et al.: "Homo sapiens mitochondrion, complete genome."
Database Genbank CDS 4468..5511 NADH dehydrogenase subunit 2 May 6, 1999, Wise,C.A et al.: "Homo sapiens NADH dehydrogenase subunit 2 (ND2) gene" XP002498795 retrieved from STN Database accession No. AF014899.
Davis et al, "Selfotel in acute ischemic stroke possible neurotoxic effects of an NMDA antagonist", Stroke, 31:347-354, (2000).
Dawson et al, "Nitric oxide mediates glutamate neurotoxicity in primary cortical cultures", Proc. Natl. Acad. Sci. USA, 88:6368-6371, (1991).
Dingledine et al, "The glutamate receptor ion channels", Pharmacological Reviews, 51(1):7-61, (1999).
European Supplementary Search Report of Feb. 9, 2011 for EP 07800509.7.
Fearnley et al, "Conservation of sequences of subunits of mitochondria! complex I and their relationships with other proteins", Biochimica et Biophysica Acta, 1140:105-134 (1992).

(Continued)

Primary Examiner — Christine J Saoud
Assistant Examiner — Jon M Lockard
(74) Attorney, Agent, or Firm — Alston & Bird LLP

(57) ABSTRACT

The present invention provides a method for ameliorating inflammatory and/or neuropathic pain in a subject by modifying the activity of N-methyl-D-aspartate (NMDA) receptors in cells of the subject by inhibition of the interaction of the unique domain of the tyrosine kinase Src enzyme and the NMDA receptor complex.

4 Claims, 16 Drawing Sheets

(56) References Cited

OTHER PUBLICATIONS

Fix et al, Neuronal vacuolization and necrosis Induced by the non-competitive N-methyl-D-aspartate (NMDA) antagonist. MK(+)801 (dizocilpine maleate): a light and electron microscopic evaluation of the rat retrosplenial cortex, *Experimental Neurology*, 123:204-215, (1993).

Friel et al, "Mitochondria as regulators of stimulus-evoked calcium signals in neurons", *Cell Calcium*, 28(516):307-316, (2000).

Gingrich et al., "Correction for Gingrich et al, PNAS, 101(16) 6237-6242 (2004)", *PNAS*, 103(25):9744, (2006).

Gingrich et al., "Unique domain anchoring of SRC to synaptic NMDA receptors via the mitochondrial protein NADH dehydrogenase subunit 2", *PNAS*, 101(16):6237-6242, (2004).

Gingrich et al., Society for Neuroscience Abstract. Program #33.14, poster location C-65, Abstract, p. 1 of 1, (2001).

Gorman et al, "Role of Mitochondria in Neuronal Apoptosis", *Developmental Neuroscience*, 22:348-358, (2000).

Guo et al, "Tyrosine phosphorylation of the NR2B subunit of the NMDA receptor in the spinal cord during the development and maintenance of inflammatory hyperalgesia" *The Journal of Neuroscience*, 22(14):6208-6217, (2002).

Guo, et al. "Tyrosine Phosphorylation of the NR2B Subunit of the NMDA Receptor in the Spinal Cord during the Development and Maintenance of Inflammatory Hyperalgesia", *J. of Neuroscience*, 22(14):6208-6217, (2002).

Gyuris et al, "Cdi1, a human G1 and S phase protein phosphatase that associates with Cdk2", *Cell*, 75:791-803, (1993).

Henderson et al, "The receptor tyrosine kinase EphB2 regulates NMDA-dependent synaptic function", Neuron, 32:1041-1056, (2001).

Hirsch et al, "A pivotal role for glutamate in the pathogenesis of schizophrenia, and its cognitive dysfunction", *Pharmacology Biochemistry and Behavior*, 56(4):797-802, (1997).

Huang et al, "CAKB/Pyk2 kinase is a signaling link for induction of long-term potentiation in CA1 hippocampus", *Neuron*, 29:485-496, (2001).

Ibrahim et al, Regulation of mitochondrial protein synthesis at the polyribosomal lever, *The Journal of Biological Chemistry*, 251(1):108-115, (1976).

Ikonomidou et al, "Why did NMDA receptor antagonists fail clinical trials for stroke and traumatic brain injury?", *The Lancet Neurology*, 1:383-386, (2002).

Ingman et al, "NADH dehydrogenase subunit 2 [*Homo sapiens*]", *Genebank*, Accession No. AAK17260, (Aug. 22, 2003).

Kandel, "The molecular biology of memory storage: a dialogue between genes and synapses", *Science*, 294:1030-1038, (2001).

Kennedy et al, Biochemical and immunochemical evidence that the 'major postsynaptic density protein' is a subunit of a calmodulin-dependent protein kinaseo. *Proc. Natl. Acad. Sci. USA*, 80(23):7357-7361, (1983).

Kramar et al, "Integrins modulate fast excitatory transmission at hippocampal synapses", *The Journal of Biological Chemistry*, 278(12):10722-10730, (2003).

Lei at al, "Platelet-derived growth factor receptor-Induced feed-forward Inhibition of excitatory transmission between hippocampal pyramidal neurons", *J. Bid. Chem.*, 274(4430617-30623, (1999).

Liu et al, "Potentiation of Carman-evoked adenosine release by an adenosine kinase inhibitor and an adenosine deaminase inhibitor in the rat hind paw: a microdialysis study", *European Journal of Pharmacology*, 408:143-152, (2000).

Liu et al, oRegulation of c-Src tyrosine kinase activity by the Sic SH2 Domain, *Oncogene*, 8:1119-1126, (1993).

Lu et al, "G-protein-coupled receptors act via protein kinase C and Src to regulate NMDA receptors", *Nature Neuroscience*, 2(4):331-338, (Apr. 1999).

Lu et al, "Src activation in the induction of long-term potentiation in CA1 hippocampal neurons", *Science*, 279:1363-1367, (1998).

Luttrell et al, "The role of beta-arrestins in the termination and transduction of G-protein-coupled receptor signals", *Journal of Cell Science*, 115:455-465, (2002).

MacDonald et al, "Regulation of N-methyl-D-aspartate receptors revealed by intracellular dialysis of murine neurones in culture", *Journal of Physiology*, 414:17-34 (1989).

Malenka et al, "Long-term potentiation—a decade of progress?", *Science*, 285:1870-1874, (1999).

Mariottini et al, "Identification of the polypeptides encoded in the unassigned reading frames 2, 4. 4L, and 5 of human mitochondrial DNA", *Proc. Natl. Acad. Sci. USA*, 83:1563-1587, (1986).

Marusich et al, 'Expression of mtDNA and riDNA encoded respiratory chain proteins in chemically and genetically-derived RhoO human fibroblasts:a comparison at subunit proteins in normal fibroblasts treated with ethicium bromide and fibroblasts from a patent with mtDNA depletion syndrome', *Biochimica at Biophysics Acta*, 1382:145-159, (1997).

Mattson, Apoptosis in neurodegenerative disorders, *Nature Reviews—Molecular Cell Biology*, 1:120-129, (2000).

Morris at al, Failure of the competitive N-rnethyl-D-aspartate antagonist Selfotel (CGS 19755) in the treatment of severe head injury: results of two Phase III clinical trials, *J. Neurosurg.*, 91:737-743, (1999).

Murai at al, "Can Eph receptors stimulate the mind?", *Neuron*, 33:159-162, (2002).

Ngo et al., "Computational complexity, protein structure prediction, and the Levinthal paradox" *The Protein Folding Problem and Tertiary Structure Prediction*, In Merz and Le Grand (Eds.) Birkhauser:Boston, pp. 491-495, (1994).

Pawson, "Protein modules and signaling networks", *Nature*, 373:573-580, (1995).

Pei at al, "Transient cerebral ischemia increases tyrosine phosphorylation of the synaptic RAS-GTPase activating protein, SynGAP", *Journal of Cerebral Blood Flow and Metabolism*, 21:955-963, (2001).

Pelkey et al, "Tyrosine phosphatase STEP is a tonic brake on induction of long-term potentiation", *Neuron*, 34:127-138, (2002).

Petralia et al, oSelective acquisition of AMPA receptors over post-natal development suggests a molecular basis for silent synapses, *Nature Neuroscience*, 2(1):31-36, (1999).

Planells-Cases et al, "Small molecules targeting the NMDA receptor complex as drugs for neuropathic pain", *Mini Reviews in Medicinal Chemistry*, 3:749-756, (2003).

Ramachandran et al, "Inhibition of mitochondria! protein synthesis results in increased endothelial cell susceptibility to nitric oxide-Induced apoptosis", *Proc. Natl. Acad. Sci. USA*, 99(10):6643-6648, (2002).

Reers et al, "J-aggregate formation of a carbocyanine as a quantitative fluorescent indicator of membrane potential", *Biochemistry*, 30:4480-4486, (1991).

Rizzuto, "Intracellular Ca2+ pools in neuronal signaling", *Current Opinion in Neurobiology*, 11:306-311, (2001).

Salter et al., "SRC Kinases: A hub for NMDA receptor regulation", *Nature Reviews*, 5:317-328, (2004).

Sanna et al, "A role for Src kinase in spontaneous epileptiform activity in the CA3 region of the hippocampus", *Proc. Natl. Acad. Sci. USA*, 97(15):8653-8657, (2000).

Sans et al, "A developmental change in NMDA receptor-associated proteins at hippocampal synapses", *Journal of Neuroscience*, 20(3)1260-1271, (2000).

Sazanov et al, "Cryo-electron crystallography of two sub-complexes of bovine complex I reveals the relationship between the membrane and peripheral arms", *J. Mot. Biol.*, 302:455-464, (2000).

Sazanov et al, "Resolution of the membrane domain of bovine complex I into subcomplexes: Implications for the structural organization of the enzyme", *Biochemistry*, 39:7229-7235, (2000).

Scannevin et al, "Postsynaptic organization and regulation of excitatory synapses" *Nature Reviews Neuroscience*, 1:133-141, (2000).

Schwarze et al., *Nature*, 285:1569-1572, (1999).

Sheng et al, "LIgand-gated ion channel interactions with cytoskeletal and signaling proteins", *Annu. Rev. Physiol.*, 62:755-778, (2000).

Sheng et al, "Postsynaptic signaling and plasticity mechanisms", *Science*, 298:776-780, (2002).

(56) References Cited

OTHER PUBLICATIONS

Shepherd at al, "Three-dimensional structure and composition of CA3-CA1 axons in rat hippocampal slices: implications for presynaptic connectivity and compartmentalization", *The Journal of Neuroscience*, 18(20):8300-8310, (1998).
Siekevitz, "The postsynaptic density: a possible role in long-lasting effects in the central nervous system", *Proc. Natl. Acad. Sci. USA*, 82:3494-3498, (1985).
Simon et al, "Blockade of N-methyl-D-aspartate receptors may protect against ischemic damage in the brain", *Science*, 226:850-852, (1984).
Smart, "Regulation of excitatory and inhibitory neurotransmitter-gated ion channels by protein phosphorylation", *Current Opinion in Neurobiology*, 7:358-367, (1997).
Soltys et al, "Mitochondrial proteins at unexpected cellular locations: export of proteins from mitochondria from an evolutionary perspective", *International Review of Cytology*, 194:133-196, (1999).
Soltys et al, *Trends in Biochemical Science*, 24:174-177, (1999).
Takasu et al, "Modulation of NMDA receptor-dependent calcium influx and gene expression through EphB receptors", *Science*, 295:491-495, (2002).
Thornton et al., "H-Ras modulates N-methyl-D-aspartate receptor function via inhibition of Src tyrosine kinase activity." *The Journal of Biological Chemistry*, 278(26):23823-23829, (2003).
U.S. Appl. No. 11/512,802, Final Rejection mailed May 11, 2010.
U.S. Appl. No. 11/512,802, Non-Final Rejection mailed Mar. 2, 2009.
U.S. Appl. No. 11/512,802, Non-Final Rejection mailed Oct. 28, 2009.
U.S. Appl. No. 11/512,802, Notice of Allowance mailed Mar. 16, 2011.
U.S. Appl. No. 11/512,802, Notice of Allowance mailed Nov. 5, 2010.
U.S. Appl. No. 11/512,802, Requirement for Restriction/Election mailed Aug. 11, 2008.
U.S. Appl. No. 10/814,109 Non-Final Office Action mailed Sep. 11, 2006.
U.S. Appl. No. 10/814,109 Notice of Allowance mailed May 13, 2008.
U.S. Appl. No. 10/814,109 Restriction Requirement mailed May 1, 2006.
Viviani et al., "Interleukin-1beta enhances NMDA receptor-mediated intracellular calcium increase through activation of the Src family of kinases," *The Journal of Neuroscience*, 23(25):8692-8700, (2003).
Walikonis et al, "Identification of proteins in the postsynaptic density fraction by mass spectrometry", *Journal of Neuroscience*, 20(11):4069-4080, (2000).
Walker, "The NADH:ubiquinone oxidoreductase (complex I) of respiratory chains", *Quarterly Reviews of Biophysics*, 25(3):253-324, (1992).
Wang et al, "Regulation of NMDA receptors by tyrosine kinases and phosphatases", *Nature*, 369:233-235, (1994).
Wells, J.A., "Additivity of mutational effects in proteins," *Biochemistry*, 29(37):8509-8517, (1990).
Wu et al, The synthesis of ATP by glycolytic enzymes in the postaynaptic density and the effect of endogenously generated nitric oxide, *Proc. Natl. Acad. Sci. USA*, 94:13273-13278 (1997).
Yu et al, "Gain control of NMDA-receptor currents by intracellualr sodium", *Nature*, 396:469-473, (1998).
Yu et al, "NMDA channel regulation by channel-associated protein tyrosone kinase Src", *Science*, 275:674-677, (1997).
U.S. Appl. No. 13/426,488, Notice of Allowance and Fees Due mailed Mar. 9, 2012.
EPO Application No. EP 05729989.3, Supplementary European Search Report, mailed Oct. 21, 2008.
U.S. Appl. No. 13/165,764, Notice of Allowance mailed Dec. 19, 2011.
WIPO Application No. PCT/CA2005/000477, International Preliminary Report on Patentability, issued Oct. 4, 2006.
WIPO Application No. PCT/CA2005/000477, International Search Report, mailed Jul. 28, 2005.
WIPO Application No. PCT/CA2005/000477, Written Opinion of the International Searching.Authority, mailed Jul. 28, 2005.
WIPO Application No. PCT/CA2007/001483, International Preliminary Report on Patentability, issued Oct. 4, 2006.
WIPO Application No. PCT/CA2007/001483, International Search Report, mailed Dec. 27, 2007.
WIPO Application No. PCT/CA2007/001483, Written Opinion of the International Searching Authority, mailed Dec. 27, 2007.

FIG. 2A
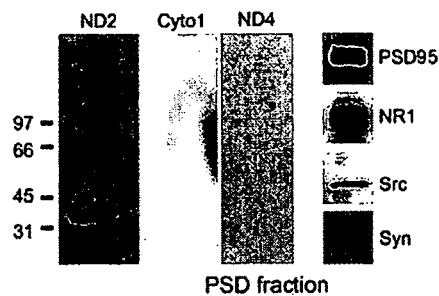
FIG. 2B
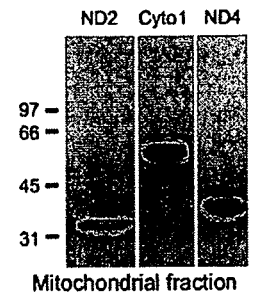
FIG. 2C
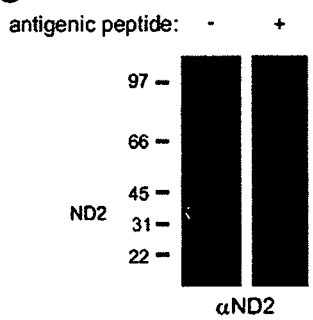
FIG. 2D
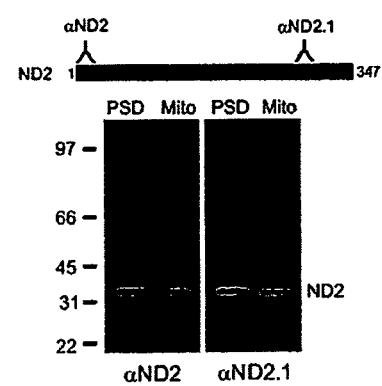
FIG. 2E
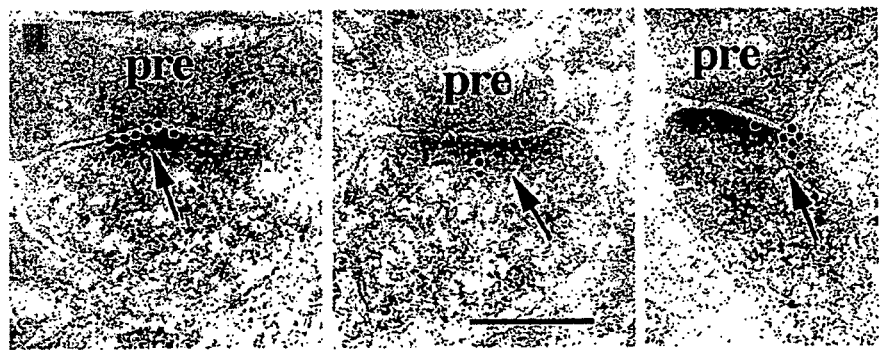
FIGURES 2A – 2E

FIG. 6A
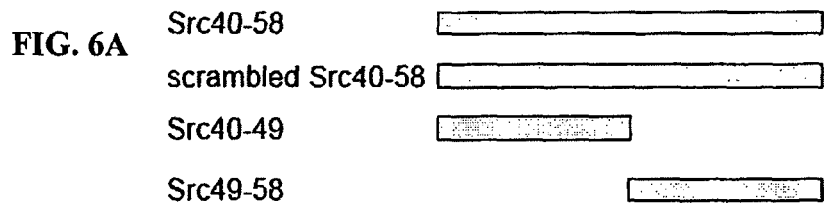
FIG. 6B
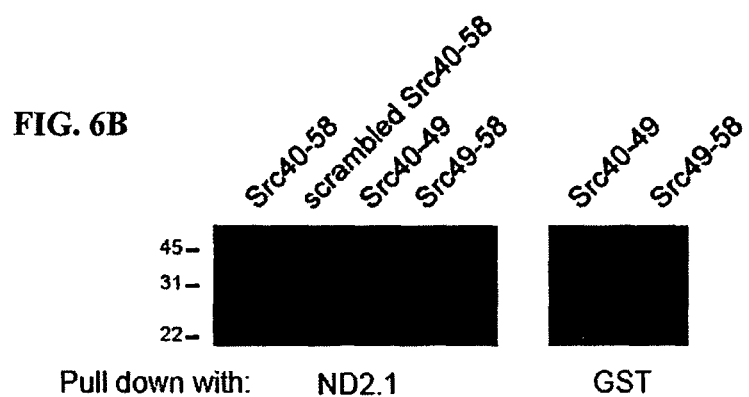
FIG. 6C
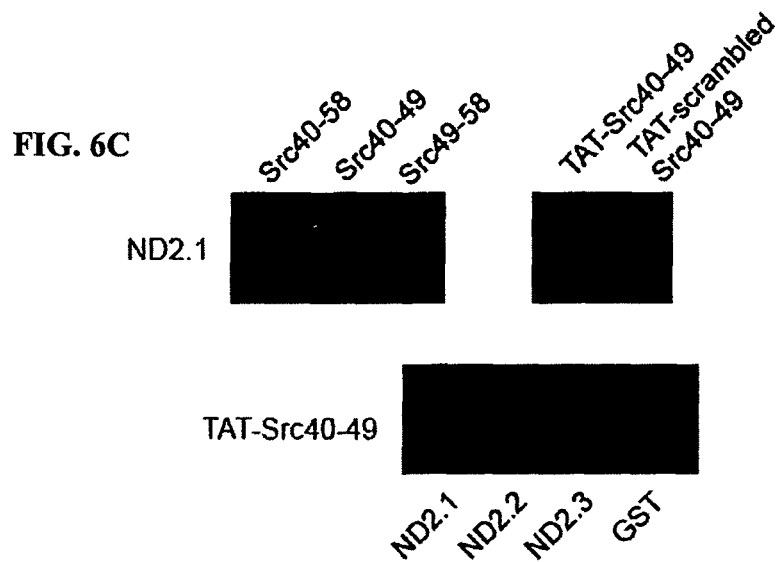
FIGURES 6A – 6C

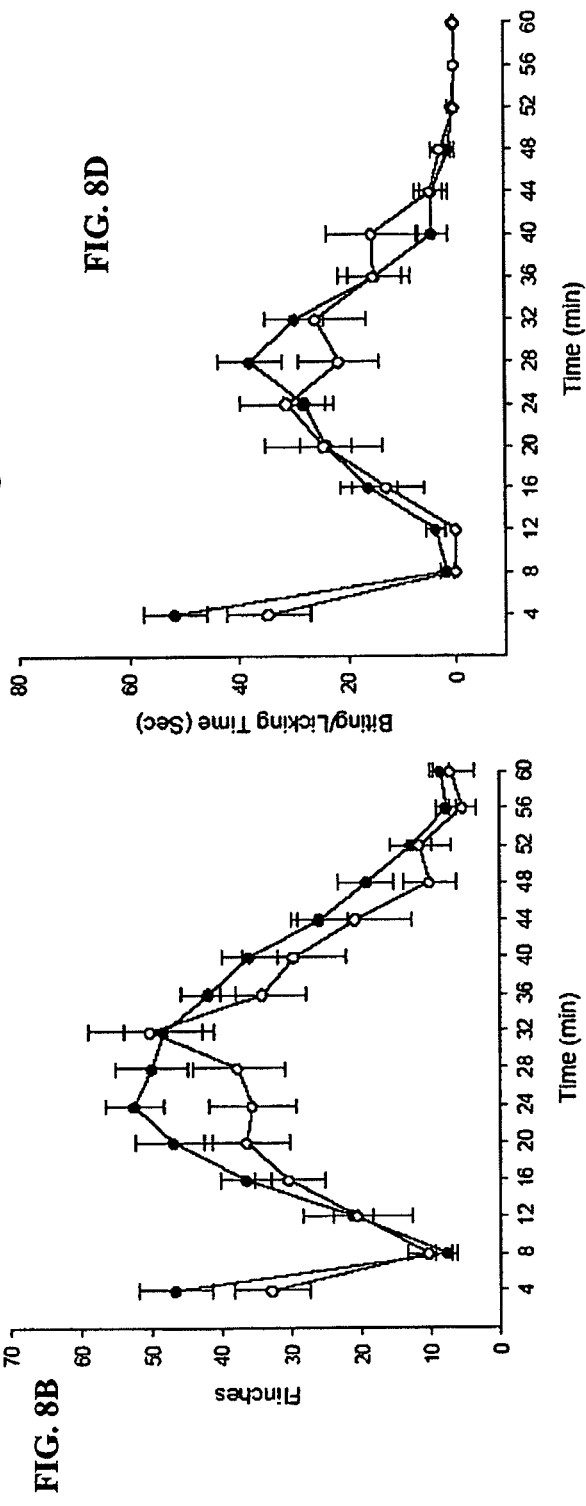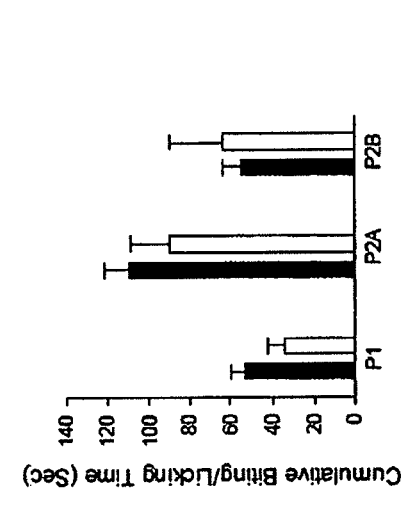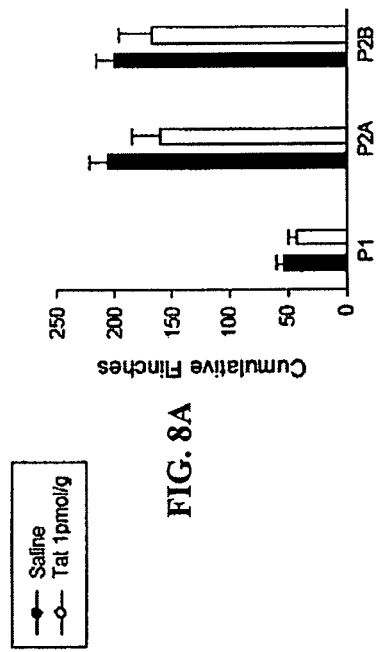
FIGURES 8A – 8D

FIG. 9A

(715) tgactaacac ccttaattcc atccaccctc ctctccctag gaggcctgcc
      cccgctaacc ggcttttgc ccaaatggac cattatcgaa gaattcacaa
      aaacaatag cctcatcatc cccaccatca tagccaccat caccctcctt
      aacctctact tctacctacg cctaatctac tccacctcaa tcacactact
      cccatatct aacaacgtaa aataaaatg acagttt (951)

FIG. 9B

(239) WLTPLIPSTL LSLGGLPPLT GFLPKWTIIE EFTKNNSLII PTIMATITLL
      NLYFYLRLIY STSITLLPMS NNVKMKWQFE (321)

FIGURES 9A-9B

FIG. 14A
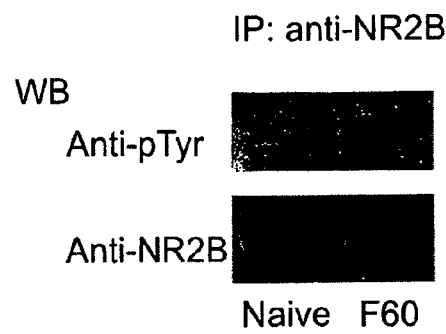
FIG. 14B
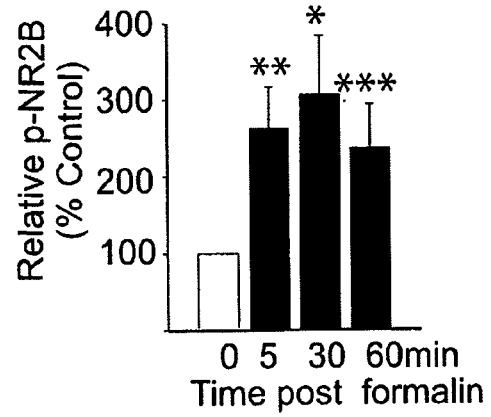
FIG. 14C
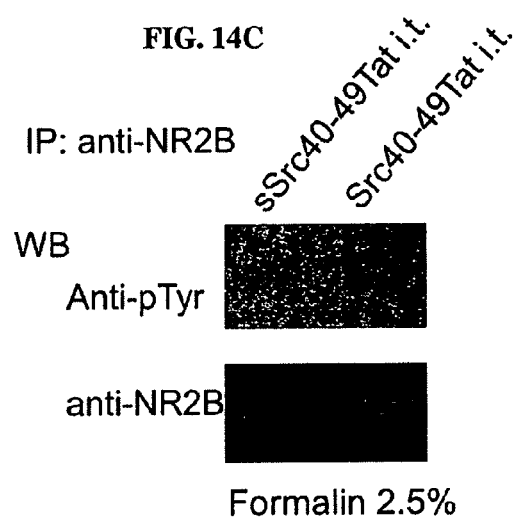
FIG. 14D
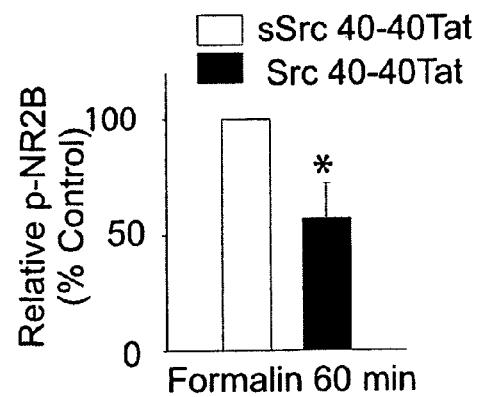
FIGURES 14A-14D

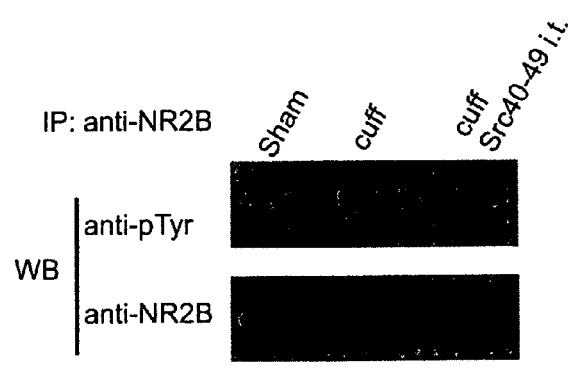
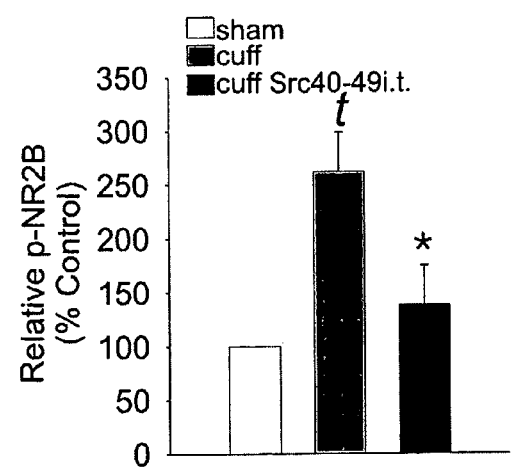
FIG. 15A
FIG. 15B
FIGURES 15A-15B

SEQUENCE LISTING

```
<160> NUMBER OF SEQ ID NOS: 13

<210> SEQ ID NO 1
<211> LENGTH: 9
<212> TYPE: PRT
<213> ORGANISM: Homo sapiens

<400> SEQUENCE: 1

Lys Pro Ala Ser Ala Asp Gly His Arg
1               5

<210> SEQ ID NO 2
<211> LENGTH: 20
<212> TYPE: PRT
<213> ORGANISM: Homo sapiens

<400> SEQUENCE: 2

Tyr Gly Arg Lys Lys Arg Arg Gln Arg Arg Lys Pro Ala Ser Ala
1               5                   10                  15

Asp Gly His Arg
            20

<210> SEQ ID NO 3
<211> LENGTH: 4145
<212> TYPE: DNA
<213> ORGANISM: Homo sapiens

<400> SEQUENCE: 3
caaacaagtg cggccatttc accagcccag gctggcttct gctgttgact ggctgtggca      60
cctcaagcag cccctttccc ctctagcctc agtttatcac cgcaagagct accattcatc     120
tagcacaacc tgaccatcct cacactggtc agttccaacc ttcccaggaa tcttctgtgg     180
ccatgttcac tccggtttta cagaacagag aacagaagct cagagaagtg aagcaacttg     240
cccagctatg agagacagag ccaggatttg aaaccagatg aggacgctga ggcccagaga     300
gggaaagcca cttgcctagg gacacacagc ggggagaggt ggagcagggc ctctatttcg     360
agacccctga ctccacacct ggtgtttgtg ccaagacccc aggctgcctc ccaggtcctc     420
tgggacagcc cctgccttct accaggacca tgggtagcaa caagagcaag cccaaggatg     480
ccagccagcg gcgccgcagc ctggagcccg ccgagaacgt gcacggcgct ggcggggggcg     540 ctttccccgc ctcgcagacc cccagcaagc cagcctcggc cgacgccac cgcggccca      600 gcgcggcctt cgcccccgcg gccgccgagc ccaagctgtt cggaggcttc aactcctcgg     660
```

```
acaccgtcac ctccccgcag agggcgggcc cgctggccgg tggagtgacc acctttgtgg      720
ccctctatga ctatgagtct aggacggaga cagacctgtc cttcaagaaa ggcgagcggc      780
tccagattgt caacaacaca gagggagact ggtggctggc ccactcgctc agcacaggac      840
agacaggcta catccccagc aactacgtgg cgccctccga ctccatccag gctgaggagt      900
ggtattttgg caagatcacc agacgggagt cagagcggtt actgctcaat gcagagaacc      960
cgagagggac cttcctcgtg cgagaaagtg agaccacgaa aggtgcctac tgcctctcag     1020
tgtctgactt cgacaacgcc aagggcctca acgtgaagca ctacaagatc cgcaagctgg     1080
acagcggcgc cttctacatc acctcccgca cccagttcaa cagcctgcag cagctggtgg     1140
cctactactc caaacacgcc gatggcctgt gccaccgcct caccaccgtg tgccccacgt     1200
ccaagccgca gactcagggc ctggccaagg atgcctggga gatccctcgg gagtcgctgc     1260
ggctggaggt caagctgggc cagggctgct ttggcgaggt gtggatgggg acctggaacg     1320
gtaccaccag ggtggccatc aaaaccctga agcctggcac gatgtctcca gaggccttcc     1380
tgcaggaggc ccaggtcatg aagaagctga ggcatgagaa gctggtgcag ttgtatgctg     1440
tggtttcaga ggagcccatt tacatcgtca cggagtacat gagcaagggg agtttgctgg     1500
actttctcaa gggggagaca ggcaagtacc tgcggctgcc tcagctggtg gacatggctg     1560
ctcagatcgc ctcaggcatg cgtacgtgg agcggatgaa ctacgtccac cgggaccttc     1620
gtgcagccaa catcctggtg ggagagaacc tggtgtgcaa agtggccgac tttgggctgg     1680
ctcggctcat tgaagacaat gagtacacgg cgcggcaagg tgccaaattc cccatcaagt     1740
ggacggctcc agaagctgcc ctctatggcc gcttcaccat caagtcggac gtgtggtcct     1800
tcgggatcct gctgactgag ctcaccacaa agggacgggt gccctaccct gggatggtga     1860
accgcgaggt gctggaccag gtggagcggg gctaccggat gcctgcccg ccggagtgtc     1920 ccgagtccct gcacgacctc atgtgccagt gctggcggaa ggagcctgag gagcggccca     1980
ccttcgagta cctgcaggcc ttcctggagg actacttcac gtccaccgag ccccagtacc     2040
agcccgggga gaacctctag gcacaggcgg gcccagaccg gcttctcggc ttggatcctg     2100
ggctgggtgg cccctgtctc ggggcttgcc ccactctgcc tgcctgctgt tggtcctctc     2160 tctgtgggc tgaattgcca ggggcgaggc ccttcctctt tggtggcatg aagggcctt      2220 ctggacctag ggtggcctga gagggcggtg ggtatgcgag accagcacgg tgactctgtc     2280
cagctcccgc tgtggccgca cgcctctccc tgcactccct cctggagctc tgtgggtctc     2340
tggaagagga accaggagaa gggctggggc cggggctgag ggtgcccttt ccagcctca      2400 gcctactccg ctcactgaac tccttcccca cttctgtgcc accccggtc tatgtcgaga      2460 gctggcaaa gagcctttcc aaagaggagc gatgggcccc tggccccgcc tgcctgccac     2520
cctgcccctt gccatccatt ctggaaacac ctgtaggcag aggctgccga gacagaccct     2580
ctgccgctgc ttccaggctg gcagcacaa ggccttgcct ggcctgatga tggtgggtgg     2640
gtgggatgag taccccctca aaccctgccc tccttagacc tgagggaccc ttcgagatca     2700
tcacttcctt gccccccattt cacccatggg gagacagttg agagcgggga tgtgacatgc     2760
ccaaggccac ggagcagttc agagtggagg cgggcttgga acccgtgct ccctctgtca      2820 tcctcaggaa ccaacaattc gtcggaggca tcatggaaag actgggacag cccaggaaac     2880
aaggggtctg aggatgcatt cgagatggca gattccccact gccgctgccc gctcagccca     2940
gctgttggga acagcatgga ggcagatgtg gggctgagct ggggaatcag ggtaaaaggt     3000
```

-continued

```
gcaggtgtgg agagagaggc ttcaatcggc ttgtgggtga tgtttgacct tcagagccag    3060
ccggctatga aagggagcga gcccctcggc tctggaggca atcaagcaga catagaagag    3120
ccaagagtcc aggaggccct ggtcctggcc tccttcccg  tactttgtcc cgtggcattt    3180
caattcctgg ccctgttctc ctccccaagt cggcacccct taactcatga ggagggaaaa    3240
gagtgcctaa gcggggggtga agaggacgt  gttacccact gccatgcacc aggactggct    3300
gtgtaacctt gggtggcccc tgctgtctct ctgggctgca gagtctgccc cacatgtggc    3360
catggcctct gcaactgctc agctctggtc caggccctgt ggcaggacac acatggtgag    3420
cctagccctg ggacatcagg agactgggct ctggctctgt tcggcctttg ggtgtgtggt    3480
ggattctccc tgggcctcag tgtgcccatc tgtaaagggg cagctgacag tttgtggcat    3540
cttgccaagg gtccctgtgt gtgtgtatgt gtgtgcatgt gtgcgtgtct ccatgtgcgt    3600
ccatatttaa catgtaaaaa tgtcccccc  gctccgtccc caaacatgt  tgtacatttc    3660 accatggccc cctcatcata gcaataacat tcccactgcc aggggttctt gagccagcca    3720
ggccctgcca gtggggaagg aggccaagca gtgcctgcct atgaaatttc aacttttcct    3780
ttcatacgtc tttattaccc aagtcttctc ccgtccattc cagtcaaatc tgggctcact    3840
caccccagcg agctctcaaa tccctctcca actgcctaag gcccttttgtg taaggtgtct    3900 taatactgtc ctttttttt ttttaacagt gttttgtaga tttcagatga ctatgcagag    3960
gcctggggga cccctggctc tgggccgggc ctggggctcc gaaattccaa ggcccagact    4020 tgcgggggt  ggggggtat  ccagaattgg ttgtaaatac tttgcatatt gtctgattaa    4080
acacaaacag acctcagaaa aaaaaaaaaa aaaaaaaaa  aaaaaaaaa  aaaaaaaaa     4140 aaaaa                                                                4145
```

<210> SEQ ID NO 4
<211> LENGTH: 535
<212> TYPE: PRT
<213> ORGANISM: Homo sapiens

<400> SEQUENCE: 4

```
Gly Ser Asn Lys Ser Lys Pro Lys Asp Ala Ser Gln Arg Arg Arg Ser
1               5                  10                  15

Leu Glu Pro Ala Glu Asn Val His Gly Ala Gly Gly Gly Ala Phe Pro
            20                  25                  30

Ala Ser Gln Thr Pro Ser Lys Pro Ala Ser Ala Asp Gly His Arg Gly
        35                  40                  45

Pro Ser Ala Ala Phe Ala Pro Ala Ala Ala Glu Pro Lys Leu Phe Gly
    50                  55                  60

Gly Phe Asn Ser Ser Asp Thr Val Thr Ser Pro Gln Arg Ala Gly Pro
65                  70                  75                  80

Leu Ala Gly Gly Val Thr Thr Phe Val Ala Leu Tyr Asp Tyr Glu Ser
                85                  90                  95

Arg Thr Glu Thr Asp Leu Ser Phe Lys Lys Gly Glu Arg Leu Gln Ile
            100                 105                 110

Val Asn Asn Thr Glu Gly Asp Trp Trp Leu Ala His Ser Leu Ser Thr
        115                 120                 125

Gly Gln Thr Gly Tyr Ile Pro Ser Asn Tyr Val Ala Pro Ser Asp Ser
    130                 135                 140

Ile Gln Ala Glu Glu Trp Tyr Phe Gly Lys Ile Thr Arg Arg Glu Ser
145                 150                 155                 160

Glu Arg Leu Leu Leu Asn Ala Glu Asn Pro Arg Gly Thr Phe Leu Val
```

```
                165                 170                 175
Arg Glu Ser Glu Thr Thr Lys Gly Ala Tyr Cys Leu Ser Val Ser Asp
            180                 185                 190

Phe Asp Asn Ala Lys Gly Leu Asn Val Lys His Tyr Lys Ile Arg Lys
            195                 200                 205

Leu Asp Ser Gly Gly Phe Tyr Ile Thr Ser Arg Thr Gln Phe Asn Ser
            210                 215                 220

Leu Gln Gln Leu Val Ala Tyr Tyr Ser Lys His Ala Asp Gly Leu Cys
225                 230                 235                 240

His Arg Leu Thr Thr Val Cys Pro Thr Ser Lys Pro Gln Thr Gln Gly
            245                 250                 255

Leu Ala Lys Asp Ala Trp Glu Ile Pro Arg Glu Ser Leu Arg Leu Glu
            260                 265                 270

Val Lys Leu Gly Gln Gly Cys Phe Gly Glu Val Trp Met Gly Thr Trp
            275                 280                 285

Asn Gly Thr Thr Arg Val Ala Ile Lys Thr Leu Lys Pro Gly Thr Met
            290                 295                 300

Ser Pro Glu Ala Phe Leu Gln Glu Ala Gln Val Met Lys Lys Leu Arg
305                 310                 315                 320

His Glu Lys Leu Val Gln Leu Tyr Ala Val Val Ser Glu Glu Pro Ile
                325                 330                 335

Tyr Ile Val Thr Glu Tyr Met Ser Lys Gly Ser Leu Leu Asp Phe Leu
                340                 345                 350

Lys Gly Glu Thr Gly Lys Tyr Leu Arg Leu Pro Gln Leu Val Asp Met
                355                 360                 365

Ala Ala Gln Ile Ala Ser Gly Met Ala Tyr Val Glu Arg Met Asn Tyr
            370                 375                 380

Val His Arg Asp Leu Arg Ala Ala Asn Ile Leu Val Gly Glu Asn Leu
385                 390                 395                 400

Val Cys Lys Val Ala Asp Phe Gly Leu Ala Arg Leu Ile Glu Asp Asn
                405                 410                 415

Glu Tyr Thr Ala Arg Gln Gly Ala Lys Phe Pro Ile Lys Trp Thr Ala
                420                 425                 430

Pro Glu Ala Ala Leu Tyr Gly Arg Phe Thr Ile Lys Ser Asp Val Trp
            435                 440                 445

Ser Phe Gly Ile Leu Leu Thr Glu Leu Thr Thr Lys Gly Arg Val Pro
            450                 455                 460

Tyr Pro Gly Met Val Asn Arg Glu Val Leu Asp Gln Val Glu Arg Gly
465                 470                 475                 480

Tyr Arg Met Pro Cys Pro Pro Glu Cys Pro Glu Ser Leu His Asp Leu
                485                 490                 495

Met Cys Gln Cys Trp Arg Lys Glu Pro Glu Glu Arg Pro Thr Phe Glu
            500                 505                 510

Tyr Leu Gln Ala Phe Leu Glu Asp Tyr Phe Thr Ser Thr Glu Pro Gln
            515                 520                 525

Tyr Gln Pro Gly Glu Asn Leu
530                 535

<210> SEQ ID NO 5
<211> LENGTH: 10
<212> TYPE: PRT
<213> ORGANISM: Artificial
<220> FEATURE:
<223> OTHER INFORMATION: src-activating peptide, used as a control
<220> FEATURE:
```

```
<221> NAME/KEY: MOD_RES
<222> LOCATION: (4)..(4)
<223> OTHER INFORMATION: PHOSPHORYLATION

<400> SEQUENCE: 5

Glu Pro Gln Tyr Glu Glu Ile Pro Ile Ala
1               5                   10

<210> SEQ ID NO 6
<211> LENGTH: 237
<212> TYPE: DNA
<213> ORGANISM: Homo sapiens

<400> SEQUENCE: 6
tgactaacac ccttaattcc atccaccctc ctctccctag gaggcctgcc cccgctaacc      60 ggcttttttgc ccaaatggac cattatcgaa gaattcacaa aaaacaatag cctcatcatc    120
cccaccatca tagccaccat caccctcctt aacctctact tctacctacg cctaatctac    180
tccacctcaa tcacactact ccccatatct aacaacgtaa aaataaaatg acagttt      237

<210> SEQ ID NO 7
<211> LENGTH: 80
<212> TYPE: PRT
<213> ORGANISM: Homo sapiens

<400> SEQUENCE: 7

Trp Leu Thr Pro Leu Ile Pro Ser Thr Leu Leu Ser Leu Gly Gly Leu
1               5                   10                  15

Pro Pro Leu Thr Gly Phe Leu Pro Lys Trp Thr Ile Ile Glu Glu Phe
            20                  25                  30

Thr Lys Asn Asn Ser Leu Ile Ile Pro Thr Ile Met Ala Thr Ile Thr
        35                  40                  45

Leu Leu Asn Leu Tyr Phe Tyr Leu Arg Leu Ile Tyr Ser Thr Ser Ile
    50                  55                  60

Thr Leu Leu Pro Met Ser Asn Asn Val Lys Met Lys Trp Gln Phe Glu
65                  70                  75                  80

<210> SEQ ID NO 8
<211> LENGTH: 1044
<212> TYPE: DNA
<213> ORGANISM: Homo sapiens

<400> SEQUENCE: 8
attaatcccc tggcccaacc cgtcatctac tctaccatct ttgcaggcac actcatcaca      60
gcgctaagct cgcactgatt ttttacctga gtaggcctag aaataaacat gctagctttt    120
attccagttc taaccaaaaa aataaaccct cgttccacag aagctgccat caagtatttc    180
ctcacgcaag caaccgcatc cataatcctt ctaatagcta tcctcttcaa caatatactc    240
tccggacaat gaaccataac caatactacc aatcaatact catcattaat aatcataata    300
gctatagcaa taaaactagg aatagccccc tttcacttct gagtcccaga ggttacccaa    360
ggcacccctc tgacatccgg cctgcttctt ctcacatgac aaaaactagc ccccatctca    420
atcatatacc aaatctctcc ctcactaaac gtaagccttc tcctcactct ctcaatctta    480
tccatcatag caggcagttg aggtggatta accagaccca gctacgcaa atcttagca     540 tactcctcaa ttacccacat aggatgaata atagcagttc taccgtacaa ccctaacata    600
accattctta atttaactat ttatattatc ctaactacta ccgcattcct actactcaac    660
ttaaactcca gcaccacgac cctactacta tctcgcacct gaaacaagct aacatgacta    720
```

-continued

```
acacccttaa ttccatccac cctcctctcc ctaggaggcc tgccccgct aaccggcttt      780 ttgcccaaat gggccattat cgaagaattc acaaaaaaca atagcctcat catcccacc      840 atcatagcca ccatcaccct ccttaacctc tacttctacc tacgcctaat ctactccacc     900
tcaatcacac tactccccat atctaacaac gtaaaaataa aatgacagtt tgaacataca    960
aaacccaccc cattcctccc cacactcatc gcccttacca cgctactcct acctatctcc   1020
ccttttatac taataatctt atag                                         1044
```

<210> SEQ ID NO 9
<211> LENGTH: 347
<212> TYPE: PRT
<213> ORGANISM: Homo sapiens

<400> SEQUENCE: 9

```
Met Asn Pro Leu Ala Gln Pro Val Ile Tyr Ser Thr Ile Phe Ala Gly
1               5                   10                  15

Thr Leu Ile Thr Ala Leu Ser Ser His Trp Phe Phe Thr Trp Val Gly
            20                  25                  30

Leu Glu Met Asn Met Leu Ala Phe Ile Pro Val Leu Thr Lys Lys Met
        35                  40                  45

Asn Pro Arg Ser Thr Glu Ala Ala Ile Lys Tyr Phe Leu Thr Gln Ala
    50                  55                  60

Thr Ala Ser Met Ile Leu Leu Met Ala Ile Leu Phe Asn Asn Met Leu
65                  70                  75                  80

Ser Gly Gln Trp Thr Met Thr Asn Thr Asn Gln Tyr Ser Ser Leu
                85                  90                  95

Met Ile Met Met Ala Met Ala Met Lys Leu Gly Met Ala Pro Phe His
            100                 105                 110

Phe Trp Val Pro Glu Val Thr Gln Gly Thr Pro Leu Thr Ser Gly Leu
        115                 120                 125

Leu Leu Leu Thr Trp Gln Lys Leu Ala Pro Ile Ser Ile Met Tyr Gln
    130                 135                 140

Ile Ser Pro Ser Leu Asn Val Ser Leu Leu Thr Leu Ser Ile Leu
145                 150                 155                 160

Ser Ile Met Ala Gly Ser Trp Gly Gly Leu Asn Gln Thr Gln Leu Arg
                165                 170                 175

Lys Ile Leu Ala Tyr Ser Ser Ile Thr His Met Gly Trp Met Met Ala
            180                 185                 190

Val Leu Pro Tyr Asn Pro Asn Met Thr Ile Leu Asn Leu Thr Ile Tyr
        195                 200                 205

Ile Ile Leu Thr Thr Thr Ala Phe Leu Leu Leu Asn Leu Asn Ser Ser
    210                 215                 220

Thr Thr Thr Leu Leu Leu Ser Arg Thr Trp Asn Lys Leu Thr Trp Leu
225                 230                 235                 240

Thr Pro Leu Ile Pro Ser Thr Leu Leu Ser Leu Gly Gly Leu Pro Pro
                245                 250                 255

Leu Thr Gly Phe Leu Pro Lys Trp Ala Ile Ile Glu Glu Phe Thr Lys
            260                 265                 270

Asn Asn Ser Leu Ile Ile Pro Thr Ile Met Ala Thr Ile Thr Leu Leu
        275                 280                 285

Asn Leu Tyr Phe Tyr Leu Arg Leu Ile Tyr Ser Thr Ser Ile Thr Leu
    290                 295                 300

Leu Pro Met Ser Asn Asn Val Lys Met Lys Trp Gln Phe Glu His Thr
```

```
                305                 310                 315                 320
Lys Pro Thr Pro Phe Leu Pro Thr Leu Ile Ala Leu Thr Thr Leu Leu
                    325                 330                 335
Leu Pro Ile Ser Pro Phe Met Leu Met Ile Leu
                340                 345

<210> SEQ ID NO 10
<211> LENGTH: 150
<212> TYPE: DNA
<213> ORGANISM: Homo sapiens

<400> SEQUENCE: 10
tgaataatag cagttctacc gtacaaccct aacataacca ttcttaattt aactatttat      60
attatcctaa ctactaccgc attcctacta ctcaacttaa actccagcac cacgacccta     120
ctactatctc gcacctgaaa caagctaaca                                      150

<210> SEQ ID NO 11
<211> LENGTH: 51
<212> TYPE: PRT
<213> ORGANISM: Homo sapiens

<400> SEQUENCE: 11

Trp Met Met Ala Val Leu Pro Tyr Asn Pro Asn Met Thr Ile Leu Asn
1               5                   10                  15

Leu Thr Ile Tyr Ile Ile Leu Thr Thr Thr Ala Phe Leu Leu Leu Asn
                20                  25                  30

Leu Asn Ser Ser Thr Thr Thr Leu Leu Leu Ser Arg Thr Trp Asn Lys
            35                  40                  45

Leu Thr Trp
    50

<210> SEQ ID NO 12
<211> LENGTH: 564
<212> TYPE: DNA
<213> ORGANISM: Homo sapiens

<400> SEQUENCE: 12
attaatcccc tggcccaacc cgtcatctac tctaccatct ttgcaggcac actcatcaca      60
gcgctaagct cgcactgatt ttttacctga gtaggcctag aaataaacat gctagctttt     120
attccagttc taccaaaaaa aataaaccct cgttccacag aagctgccat caagtatttc     180
ctcacgcaag caaccgcatc cataatcctt ctaatagcta tcctcttcaa caatatactc     240
tccggacaat gaaccataac caatactacc aatcaatact catcattaat aatcataata     300
gctatagcaa taaaactagg aatagccccc tttcacttct gagtcccaga ggttacccaa     360
ggcacccctc tgacatccgg cctgcttctt ctcacatgac aaaaactagc ccccatctca     420
atcatatacc aaatctctcc ctcactaaac gtaagccttc tcctcactct ctcaatctta     480
tccatcatag caggcagttg aggtggatta accagaccc agctacgcaa aatcttagca      540
tactcctcaa ttacccacat agga                                            564

<210> SEQ ID NO 13
<211> LENGTH: 188
<212> TYPE: PRT
<213> ORGANISM: Homo sapiens

<400> SEQUENCE: 13

Met Asn Pro Leu Ala Gln Pro Val Ile Tyr Ser Thr Ile Phe Ala Gly
```

```
1               5                    10                   15
Thr Leu Ile Thr Ala Leu Ser Ser His Trp Phe Phe Thr Trp Val Gly
            20                  25                  30

Leu Glu Met Asn Met Leu Ala Phe Ile Pro Val Leu Thr Lys Lys Met
            35                  40                  45

Asn Pro Arg Ser Thr Glu Ala Ala Ile Lys Tyr Phe Leu Thr Gln Ala
        50                  55                  60

Thr Ala Ser Met Ile Leu Leu Met Ala Ile Leu Phe Asn Asn Met Leu
65                  70                  75                  80

Ser Gly Gln Trp Thr Met Thr Asn Thr Thr Asn Gln Tyr Ser Ser Leu
                85                  90                  95

Met Ile Met Met Ala Met Ala Met Lys Leu Gly Met Ala Pro Phe His
                100                 105                 110

Phe Trp Val Pro Glu Val Thr Gln Gly Thr Pro Leu Thr Ser Gly Leu
            115                 120                 125

Leu Leu Leu Thr Trp Gln Lys Leu Ala Pro Ile Ser Ile Met Tyr Gln
        130                 135                 140

Ile Ser Pro Ser Leu Asn Val Ser Leu Leu Leu Thr Leu Ser Ile Leu
145                 150                 155                 160

Ser Ile Met Ala Gly Ser Trp Gly Gly Leu Asn Gln Thr Gln Leu Arg
                165                 170                 175

Lys Ile Leu Ala Tyr Ser Ser Ile Thr His Met Gly
            180                 185
```

METHOD FOR AMELIORATING PAIN BY MODIFICATION OF NMDA RECEPTORS THROUGH INHIBITION OF SRC

CROSS-REFERENCE TO RELATED APPLICATIONS

This application is a continuation of application Ser. No. 13/165,764, filed Jun. 21, 2011, which is a continuation of application Ser. No. 11/512,802, filed Aug. 29, 2006, which is a continuation-in-part of application Ser. No. 10/814,109, filed on Mar. 20, 2004, the contents of all of which are herein incorporated by reference.

FIELD OF THE INVENTION

The instant invention relates generally to protein-protein interactions that regulate intra and intercellular communication; particularly to methods for modification of protein-protein interactions; and most particularly to a method for ameliorating pain in a subject by modifying the activity of NMDA (N-methyl-D-aspartate) receptors located in cells by inhibition of the interaction of the unique domain of the tyrosine kinase Src enzyme with proteins of the NMDAR complex.

BACKGROUND OF THE INVENTION

Excitatory transmission at central synapses is primarily mediated by the amino acid glutamate acting through postsynaptic ionotropic receptors (Dingledine et al. Pharmacological Review 51:7-61 1999). The N-methyl-D-aspartate receptor (NMDAR) is one such type of ionotropic glutamate receptor (Dingledine et al. Pharmacological Review 51:7-61 1999). NMDARs are multiprotein complexes located at excitatory synapses within the postsynaptic density (PSD) comprised of the core channel subunits together with associated scaffolding and regulatory proteins that control receptor localization, ionic flux through the receptor and downstream signaling events (Scannevin et al. Nature Reviews Neuroscience 1:133-141 2000; Sheng et al. Annual Review of Physiology 62:755-778 2000). NMDAR's are crucial for central nervous system (CNS) development, neuroplasticity and pathophysiology (Dingledine et al. Pharmacological Review 51:7-61 1999; Sheng et al. Science 298:776-780 2002). Multiple factors regulate NMDAR function, including dynamic cycling of protein phosphorylation and dephosphorylation at serine/threonine or tyrosine residues (Wang et al. Nature 369: 233-235 1994; Smart Current Opinion in Neurobiology 7:358-367 1997). The Src protein is one such factor that modulates the activity of the NMDARs (Yu et al. Science 275:674-678 1997; Lu et al. Science 279:1363-1368 1998; Yu et al. Nature 396:469-474 1998).

The non-receptor protein tyrosine kinase Src is a ubiquitous enzyme with key roles in diverse development, physiological and pathological processes (Brown et al. Biochim. Biophys. Acta 1287:121-149 1996). Domains identified in Src—the Src homology 3 (SH3) domain, the SH2 domain and the SH1 (catalytic) domain are signature regions that have been used to define highly-conserved protein modules found in a wide variety of signaling proteins (Pawson Nature 373: 573-580 1995). In addition to these highly-conserved regions, Src also contains a region of low sequence conservation and unknown function, termed the unique domain.

Src is highly expressed in the CNS, functioning to regulate glutamatergic neurotransmission and synaptic plasticity (Ali et al. Current Opinion in Neurobiology 11:336-342 2001; Salter and Kalia Nature Reviews:Neuroscience 5:317-328 2004)). At glutamatergic synapses, Src modulates the activity of NMDARs (Yu et al. Science 275:674-678 1997; Lu et al. Science 279:1363-1368 1998; Yu et al. Nature 396:469-474 1998). Src represents a point through which multiple signaling cascades from G-protein coupled receptors (Luttrell et al. Journal of Cell Science 115:455-465 2002), Eph receptors (Henderson et al. Neuron 32:1041-1056 2001; Takasu et al. Science 295:491-495 2002; Murai et al. Neuron 33:159-162 2002) and integrins (Lin et al. Journal of Neurophysiology 89:2874-2878 2003; Kramar et al. Journal of Biological Chemistry 278:10722-10730 2003) converge to upregulate NMDAR channel activity, thus mediating essential neuronal excitation. The upregulation of NMDAR activity by Src is necessary for long-term potentiation (LTP) of synaptic transmission at Schaffer collateral-CA1 neuron synapses in the hippocampus (Ali et al. Current Opinion in Neurobiology 11:336-342 2001), the predominant cellular model for learning and memory (Kandel Science 294:1030-1038 2001).

However, abnormal regulation of NMDARs can have numerous pathologic effects; most resulting from the production of nitric oxide, a signaling molecule which mediates excitotoxicity (Dawson et al. Proceedings of the National Academy of Science USA 88:6368 1991). NMDARS mediate ischemic brain injury, as seen, for example in stroke and traumatic injury (Simon et al. Science 226:850 1984). In addition, abnormal NMDAR regulation has been implicated in Alzheimer's disease, Parkinson's disease (Coyle et al. Science 262:689 1993), schizophrenia (Hirsch et al. Pharmacology Biochemistry and Behavior 56(4):797-802 1997), epilepsy (U.S. Pat. No. 5,914,403), glaucoma (US Application 2002 0077322 A1) and chronic pain (Guo et al. Journal of Neuroscience 22:6208-6217 2002).

Although NMDARs are implicated in numerous pathological conditions, non-selective blocking of their function is deleterious, since complete blockade of synaptic transmission mediated by NMDA receptors is known to hinder neuronal survival (Ikonomidou et al. Lancet: Neurology 1:383-386 2002; Fix et al. Experimental Neurology 123:204 1993; Davis et al. Stroke 31:347 2000; Morris et al. Journal of Neurosurgery 91:737 1999).

Additionally, inhibition of Src kinases may also have deleterious results. Since kinases play a part in the regulation of cellular proliferation, they are frequently targeted for the development of new cancer therapies.

The majority of these therapies inhibit function of the kinase catalytic domain, which is often highly conserved between distinct kinases. Thus, inhibition of Src in the CNS with a standard kinase inhibitor may cross-react with additional kinases and adversely affect normal neuronal functions.

Considering the above-mentioned deleterious effects resulting from direct blockage of NMDARs and/or indirect inhibition of NMDARs through the use of kinase inhibitors, it is clear that there remains a need in the art for a method of modifying NMDARs which can attenuate downstream NMDAR signaling, without completely blocking, ion-channel activity.

DESCRIPTION OF THE PRIOR ART

Since the NMDA receptor is critical to both normal neuronal function and pathology, there are many known methods for modification of NMDA receptors; several examples of which are noted below.

U.S. Pat. No. 5,888,996 (David Farb) discloses a method for inhibiting NMDA glutamate receptor-mediated ion channel activity by treatment with an effective amount of a derivative of pregnenolone sulfate. This patent also discloses a method for modulating/altering excitatory glutamate-mediated synaptic activity by contacting neurons with pregnenolone sulfate or a derivative of pregnenolone sulfate.

U.S. Pat. No. 5,914,403 (Nichols et al.) discloses agents capable of modifying neuroexcitation through excitatory amino acid antagonists; in particular quinolinic acid derivatives antagonistic to a glycine binding site in the NMDAR complex. The agents disclosed by Nichols et al. have anticonvulsant activity.

U.S. Pat. No. 4,994,446 (Sokolovsky et al.) discloses a drug system comprising a MK-801/PCP type drug administered in combination with/or in sequence with excitatory amino acids such as, glutamate, glycine, aspartate and analogs thereof. The excitatory amino acids facilitate binding of the drug to the NMDAR channels. This drug system has anticonvulsant activity and can alleviate brain damage due to stroke.

U.S. Pat. No. 6,653,354 (Franks et al.) discloses a method for reducing the level of NMDAR activation by use of the NMDA antagonist, xenon to inhibit synaptic plasticity. The xenon composition of Franks et al. also acts as a neuroprotectant.

US Patent Application 2002 0123510 A1 (Chenard et al.) discloses a method for treatment of traumatic brain injury (TBI) and stroke by administration of a NR2B subtype selective NMDAR antagonist in combination with either of the following agents; sodium channel antagonist, nitric oxide synthase inhibitor, glycine site antagonist, potassium channel opener, AMPA/kainate receptor antagonist, calcium channel antagonist, GABA-A receptor modulator, anti-inflammatory agent or a thrombolytic agent. These agents either protect neurons from toxic insult, inhibit inflammatory responses after brain damage or promote cerebral reperfusion after hypoxia or ischemia.

Planells-Cases et al. (Mini Review of Medicinal Chemistry 3(7):749-756 2003) disclose that small molecule antagonists of the NMDAR are useful for the treatment of neuropathic pain caused by injury to the peripheral or central nervous system.

US Patent Application 2002 0077322 A1 (George Ayoub) discloses methods for protecting neuronal cells from glutamate-induced toxicity, such as that which occurs in ischemia and glaucoma, by increasing the activity of a cannabinoid agonist which binds specifically to a cannabinoid receptor.

US Patent Application 2003 0050243 A1 (Michael Tymianski) discloses a method for inhibition of binding between NMDARs and neuronal proteins. The inhibition is created by administration of a peptide replacement of either an NMDAR or neuronal protein interaction domain. Post-synaptic density protein 95 (PSD-95) couples NMDARs to pathways mediating excitotoxicity and ischemic brain damage. The method of Tymianski involves transducing neurons with peptides that bind modular domains on either side of the NMDAR/PSD-95 interaction complex. This transduction attenuates downstream NMDAR signaling without blocking receptor activity, protects cortical neurons from ischemic insult and reduces cerebral infarction in rats exposed to transient focal cerebral ischemia. This treatment was effective in the rats when applied before or one hour after the ischemic insult. (Aarts et al. Science 298:846-850 2002) also discloses the research described in US Patent Application 2003 0050243 A1.

As is exemplified by the examples listed above, the majority of known methods for modification of NMDA receptors generally involve administration of receptor antagonists which inhibit receptor function completely. The instant inventors are the first to modify the NMDAR by inhibiting the interaction of the unique domain of the tyrosine kinase Src enzyme with NADH dehydrogenase subunit 2 (ND2); thus preventing Src upregulation of the NMDAR by preventing binding between Src and ND2.

SUMMARY OF THE INVENTION

Src-mediated upregulation of NMDAR activity is prevented by peptide fragments of the Src unique domain and by a unique domain-binding antibody (Yu at al. Science 275: 674-678 1997; Lu et al. Science 279:1363-1368 1998) leading to the hypothesis that the upregulation of NMDAR function by Src depends on an interaction between a region in the unique domain of Src and an unknown protein in the NMDAR complex (Ali et al. Current Opinion in Neurobiology 11:336-342 2001). In order to test the hypothesis, the instant inventors searched for proteins that may interact with the unique domain of Src and may thereby mediate the interaction between this kinase and NMDARs. These proteins were generally termed "SUDAPIs" (Src unique domain anchoring protein inhibitors) by the instant inventors since they anticipate that other such inhibitors may exist which exhibit identical functions.

As a result of their search, the instant inventors became the first to identify NADH dehydrogenase subunit 2 (ND2; nucleotide sequence SEQ ID NO:8 and amino acid sequence SEQ ID NO:9) as a Src unique domain-interacting protein (Gingrich et al. PNAS 101(16):6237-6242 2004). ND2 functions as an adapter protein anchoring Src to the NMDAR complex, thus permitting Src-mediated upregulation of NMDAR activity. The instant inventors identified a region of the Src unique domain which interacts with ND2; a region located approximately at amino acid positions 40-49 of the Src protein (SEQ ID NO:1). The exogeneous peptide inhibits the ability of ND2 to anchor the Src protein to the NMDAR complex. This peptide, approximately 10 amino acids in length, has been named "SUDAPI-1" by the instant inventors, since it is the first such peptide discovered which functions to inhibit the Src unique domain anchoring protein. Administration of this exogeneous peptide prevents ND2 interaction with the Src unique domain; thus inhibiting Src-mediated upregulation of NMDAR activity. Since this peptide alone cannot cross the cell membrane to enter the cellular interior, it is combined with a carrier capable of penetrating the cell membrane. Illustrative, albeit non-limiting examples of carriers are peptides derived from viral transduction domains, such as the TAT domain derived from the Human Immunodeficiency Virus (HIV) and VP22 derived from the Herpes Simplex Virus, arginine-rich peptides, fusogenic antennapedia peptides derived from Drosophilia and lipids. Lipids can facilitate crossing of the cell membrane by enclosing the peptide in a lipid vesicle or liposome (lipid transfection protocol) or the peptide can be directly modified with lipid groups. Use of the HIV-Tat domain peptide as a carrier is exemplified in the Examples described herein. SUDAPI-1 fused to the HIV-Tat domain is designated "TSUDAPI-1" (SEQ ID NO:2). The NMDAR activity is evoked by glutamate and is additionally regulated by many distinct pathways other than the Src pathway. Inhibition of Src suppresses but does not completely inhibit the NMDAR as is apparent from the electrophysiologic measurements of receptor activity shown in FIGS. 5D-F. Thus, the instant invention provides methods and compositions for modifying NMDAR function without completely blocking the receptor or adversely affecting other neuronal proteins with the use of generalized kinase inhibitors. These methods and compositions may be used to ameliorate diseases and/or other conditions related to NMDAR signaling. Illustrative, albeit non-limiting examples of such diseases and/or other conditions are stroke, hypoxia, ischemia, multiple sclerosis, Huntington's chorea, Parkinson's disease, Alzheimer's disease, hyperglycemia, diabetes, traumatic injury, epilepsy, grand mal seizures, spasticity, cerebral palsy, asthma, cardiac arrest, macular degeneration, mental diseases, schizophrenia, AIDS dementia complex, other dementias, AIDS wasting syndrome, inflammation, pain, opioid addiction, cocaine addiction, alcohol addiction, other conditions associated with substance abuse and anorexia. An example of such amelioration is illustrated in Example 7 wherein pain behaviors are reduced in rats treated with the composition of the instant invention prior to undergoing the formalin test. Furthermore, in addition to reducing inflammatory pain, the composition of the instant invention inhibits Src-mediated NMDAR upregulation-dependent neuropathic pain in rats and mice having peripheral nerve injury (Example 9).

Src upregulation of the NMDAR is involved in the pathway of long-term potentiation (LTP) (Huang et al. Neuron 29:485-496 2001; Lu et al. Science 279:1363-1367 1998). Since LTP is considered a model for learning and memory, the compositions of the instant invention are contemplated for use in methods which elucidate mechanisms of learning and memory and/or enhance learning and memory.

The NMDAR is expressed almost exclusively in neurons; however the interaction between Src and ND2 was shown to occur in multiple and diverse tissues (Example 8 and FIGS. 10A-B). Thus, the instant inventors hypothesize that the Src-ND2 interaction has functions other than regulation of NMDAR's and contemplate that the compositions of the instant invention can be used in methods for the general inhibition of Src in multiple cell types.

Accordingly, it is an objective of the instant invention to provide a method for modifying NMDAR interaction with non-receptor tyrosine kinase Src in any cell which expresses the NMDAR by providing a composition including at least one SUDAPI and administering the composition to the cell in an amount effective to achieve modification of the NMDAR interaction with non-receptor tyrosine kinase Src in the cell wherein said modification ameliorates a disease or condition related to NMDAR signaling. The methods and compositions of the instant invention are particularly suited to use with cells of the nervous system but can also be used with any cell which expresses the NMDAR.

It is another objective of the instant invention to provide a pharmaceutical composition for modifying NMDAR interaction with non-receptor tyrosine kinase Src in cells comprising at least one SUDAPI combined with a pharmacologically acceptable solution or carrier.

It is also an objective of the instant invention to provide a method for modifying NMDAR interaction with non-receptor tyrosine kinase Src in any cell which expresses the NMDAR by providing a composition including SUDAPI-1 and administering the composition to the cell in an amount effective to achieve modification of the NMDAR interaction with non-receptor tyrosine kinase Src in the cell wherein said modification ameliorates a disease or condition related to NMDAR signaling.

It is another objective of the instant invention to provide a pharmaceutical composition for modifying NMDAR interaction with non-receptor tyrosine kinase Src in cells comprising SUDAPI-1 combined with a pharmacologically acceptable solution or carrier.

It is yet another objective of the instant invention to provide a method for modifying NMDAR interaction with non-receptor tyrosine kinase Src in any cell which expresses the NMDAR by providing a composition including TSUDAPI-1 and administering the composition to the cell in an amount effective to achieve modification of the NMDAR interaction with non-receptor tyrosine kinase Src in the cell wherein said modification ameliorates a disease or condition related to NMDAR signaling.

It is still another objective of the instant invention to provide a pharmaceutical composition for modifying NMDAR interaction with non-receptor tyrosine kinase Src in cells comprising TSUDAPI-1 combined with a pharmacologically acceptable solution.

It is another objective of the instant invention to provide an isolated peptide (ND2.1; SEQ ID NO:7) which interacts with the Src unique domain to anchor Src to the NMDAR complex thus permitting Src-mediated upregulation of NMDAR activity.

It is still another objective of the instant invention to provide a method for inhibiting non-receptor tyrosine kinase Src in cells expressing non-receptor tyrosine kinase Src by providing a composition including at least one SUDAPI and administering the composition to the cells in an amount effective to achieve inhibition of non-receptor tyrosine kinase Src in the cells.

It is another objective of the instant invention to provide a pharmaceutical composition for inhibiting non-receptor tyrosine kinase Src in cells comprising at least one SUDAPI combined with a pharmacologically acceptable solution or carrier.

It is another objective of the instant invention to provide a composition useful in methods for elucidating the mechanisms of learning and memory.

It is yet another objective of the instant invention to provide a composition useful in methods for enhancing learning and memory.

It is another objective of the instant invention to provide a composition useful in methods for treating inflammatory pain.

It is yet another objective of the instant invention to provide a composition useful in methods for treating neuropathic pain.

Another objective of the instant invention is to provide a method for ameliorating inflammatory and/or neuropathic pain in a subject by modifying NMDAR interaction with non-receptor tyrosine kinase Src in any subject having cells which express the NMDAR by providing a composition including at least one SUDAPI and administering the composition to the subject in an amount effective to achieve modification of the NMDAR interaction with non-receptor tyrosine kinase Src in the cells to ameliorate pain in the subject.

It is yet another objective of the instant invention to provide a method for ameliorating inflammatory and/or neuropathic pain in a subject by modifying NMDAR interaction with non-receptor tyrosine kinase Src in cells of the subject by providing a composition including SUDAPI-1 (SEQ ID NO:1) or TSUDAPI-1 (SEQ ID NO:2) and administering the composition to the subject in an amount effective to achieve modification of the MNDAR interaction with non-receptor tyrosine kinase Src in the cells to ameliorate pain in the subject.

Other objectives and advantages of the instant invention will become apparent from the following description taken in conjunction with the accompanying drawings wherein are set forth, by way of illustration and example, certain embodiments of the instant invention. The drawings constitute a part of this specification and include exemplary embodiments of the present invention and illustrate various objects and features thereof.

Abbreviations and Definitions

The following list defines terms, phrases and abbreviations used throughout the instant specification. Although the terms, phrases and abbreviations are listed in the singular tense the definitions are intended to encompass all grammatical forms.

As used herein, the term "subject" refers to any organism having cells which express or are capable of expressing NMDA receptors.

As used herein, the term "modification" refers to any action and/or treatment which alters the function of a protein.

As used herein, the term "inhibition" refers to any action and/or treatment which operates against the full activity of a protein thus reducing and/or completely suppressing protein function.

As used herein, the term "interaction" refers to an action wherein two substances in close physical proximity act upon each other.

As used herein, the term "anchor" means to stabilize or secure firmly in place.

As used herein, the term "isolated peptide" refers to a peptide which has been "altered by the hand of man" and separated from the co-existing materials of its natural state. An isolated peptide has been changed or removed from its original environment or both.

As used herein, the abbreviation "CNS" refers to the central nervous system, which includes the brain, cranial nerves and the spinal cord.

As used herein, the abbreviation "PNS" refers to the peripheral nervous system, which is the network of nerves that connect the CNS to organs, muscles, vessels and glands. Peripheral nerve injury often results in abnormal neuropathic pain, hyperalgesia and/or allodynia.

As used herein, the term "excitatory neurotransmission" refers the passage of signals from one neuron to another via chemical substances or electrical impulses.

As used herein, the abbreviation "NMDAR" refers to the N-methyl-D-aspartate receptor, an ionotropic cation-ion specific, ligand-gated (glutamate-gated) ion channel which is activated by NMDA or NMDA-like ligands (agonist activation) such as glutamate. The NMDAR is a multi-protein complex including the core channel subunits with associated scaffolding and regulatory proteins, located in the excitatory synapses in the post-synaptic density. Activation of the receptor opens the channel to allow cations ($Ca^{+2}$, $Na^+$ and $K^+$) to cross the cellular membrane. "Upregulation of NMDAR activity" refers to the enhanced opening of the receptor ion channels.

As used herein, the term "Src" refers to a protein exhibiting tyrosine-specific kinase activity. The Src protein is involved in controlling diverse cellular functions, including regulation of NMDAR activity.

As used herein, the term "phosphorylation" refers to a reversible covalent modification wherein a phosphate group (non-protein) is attached/detached to a protein. The addition and removal of the phosphate group causes changes in the tertiary structure of the protein that alter its activity.

As used herein, the abbreviation "PSD" refers to the post-synaptic density, a specialized portion of the neuronal cytoskeleton, located near the post-synaptic membrane. The PSD provides a support matrix for signal transduction.

As used herein, the abbreviation "LTP" refers to long term potentiation, an activity-dependent persistent enhancement of synaptic transmission which is considered a model of learning and memory. The biochemical signaling cascade which results in LTP involves the activation of Src which in turn, activates NMDARs.

As used herein, the abbreviation "ND2" refers to NADH dehydrogenase subunit 2, a subunit of mitochondrial Complex I. The instant inventor was the first to recognize that ND2 is present in the PSD and acts as an adaptor protein for anchoring Src to the NMDAR complex.

As used herein, the abbreviation "SUDAPI" refers to any substance which functions as a Src unique domain anchoring protein inhibitor.

As used herein, the abbreviation "SUDAPI-1" refers to the first Src unique domain anchoring protein inhibitor discovered by the instant inventors. SUDAPI-1 is a peptide, generally 10 amino acid residues in length corresponding approximately to amino acid positions 40-49 of the Src unique domain (SEQ ID NO:1).

As used herein, the phrase "corresponding approximately to amino acid positions 40-49 of the Src unique domain" refers to the slight difference which is possible in amino acid position numbering of the Src protein due to species variations and conventions within the art regarding whether the first methionine counts as a residue or not.

As used herein, the abbreviation "TSUDAPI-1" refers to SUDAPI-1 which is combined with the carrier peptide, HIV-Tat (SEQ ID NO:2).

As used herein, the term "carrier" refers to any substance which is attached to another substance which alone cannot traverse the cell membrane to enter the cellular interior. The carrier substance functions to carry this other substance through the cellular membrane into the cellular interior. Illustrative, albeit non-limiting examples include lipids and peptides having transducing and/or fusogenic ability.

As used herein, the term "HIV-Tat" refers to the transduction domain of the human immunodeficiency virus (HIV); the causative agent of Acquired Immunodeficieny Syndrome (AIDS). HIV-Tat peptide is often used as a carrier to transport molecules into cells.

As used herein, the term "VP22" refers to a transduction domain of the herpes simplex virus. VP22 peptide is often used as a carrier to transport molecules into cells.

As used herein, the term "antennapedia" refers to peptides derived from Drosophilia which have fusogenic ability. Antennapedia peptide is often used as a carrier to transport molecules into cells.

The phrase "pharmaceutically acceptable" is used herein as described in U.S. Pat. No. 6,703,489. "Pharmaceutically acceptable" means approved by a regulatory agency or listed in a generally approved pharmacopeia for use in animals and humans. Solutions are usually preferred when a composition is administered intravenously. Illustrative, albeit non-limiting examples of pharmaceutically acceptable solutions include water, oils, saline, aqueous dextrose and glycerol.

As used herein, the phrase "amount effective" refers to an amount of a composition sufficient to elicit a change in activity of the NMDAR.

As used herein, the phrase "ameliorate a disease and/or condition" refers to an action which causes symptoms of a disease and/or condition to improve or become better.

As used herein, the phrase "ameliorating pain" refers to an action which causes pain symptoms to improve and/or disappear.

As used herein, the abbreviation "SH" refers to a Src homology domain; regions that have been used to define highly-conserved protein modules found in a wide variety of signaling proteins (T. Pawson Nature 373:573-580 1995).

As used herein, the phrase "unique domain" refers to a Src domain having low sequence conservation and unknown function.

As used herein, the abbreviation "ND4" refers to NADH degydrogenase subunit 4, an oxidoreductase protein, a component of mitochondrial Complex I (JE Walker Quarterly Reviews of Biophysics 25(3):253-324 1992; Sazanov et al. Biochemistry 39:7229-7235 2000; Sazanov et al. Journal of Molecular Biology 302:455-464 200).

As used herein, the abbreviation "NdufA9" refers to NADH-Ubiquinone Oxidoreductase 1 alpha subcomplex 9, also a subunit of mitochondrial complex I (NCBI GeneID: 4704).

As used herein, the abbreviation "Cyto 1" refers to cytochrome c oxidase subunit 1, an inner mitochondrial membrane protein that is part of Complex IV (Marusich et al. Biochim. Biophys. Acta 1362:145-159 1997).

As used herein, the abbreviation "mEPSCs" refers to miniature excitatory post-synaptic currents, a type of excitatory neurotransmission.

The terms "SUDAPI-1" and "Src40-49" are used interchangeably herein (SEQ ID NO:1).

The terms "TSUDAPI-1"; "Src40-49-Tat"; "Src40-49-HIV-Tat"; "Tat-Src40-49" and "HIV-Tat-Src40-49" are used interchangeably herein (SEQ ID NO:2).

The terms "Src40-58" and "scrambled Src40-58" are used repeatedly throughout and refer to peptides comprising amino acid residues 40-58 of SEQ ID NO:4.

The term "Src49-58" is used repeatedly throughout and refers to a peptide comprising amino acid residues 49-58 of SEQ ID NO:4.

As used herein, the term "pain" refers to an unpleasant sensation. Pain has both physical and emotional components. Pain is mediated by nerves which carry the pain impulses to the brain where their interpretation can be influenced by many factors.

As used herein, the term "inflammatory pain" refers to pain associated with inflammation. Inflammation is the nonspecific immune response of an organism to infection, irritation and/or injury. Inflammation is characterized by redness, swelling, warmth and pain. The formalin test as performed on rats in Example 7 is a model for inflammatory pain.

As used herein, the term "neuropathic pain" refers to pain directly associated with the nervous system resulting from damage to the nerves or other changes in the nervous system. Neuropathic pain is associated with changes in sensory processing (for example, with temperature and touch) and occurs without inflammation. The cuff-implantation in mice as exemplified in Example 9 is a model for neuropathic pain.

As used herein, the term "allodynia" refers to pain caused by a stimulus that does not normally result in a pain response. Allodynia involves a change in the quality of a sensation or a loss of specificity of a sense, i.e. a first response to a stimulus is not pain, but a next response to the stimulus results in pain. Tactile allodynia is pain that results from a non-injurious stimulus to the skin, such as a light touch.

As used herein, the abbreviation "PWT" refers to paw withdrawal threshold, a measurement of pain sensitivity in animals, in particular, rats and mice. Threshold is measured in terms of force. A reduction in threshold suggests the development of allodynia.

As used herein, the term "nociceptor" refers to a specialized type of nerve cell that senses and responds to pain.

As used herein, the term "hyperalgesia" refers to a condition of altered perception such that stimuli which would normally induce a trivial discomfort cause significant pain. Hyperalgesia can be caused by damage to nociceptors present in tissue.

As used herein, the term "transgenic animal" refers to an animal whose genome has been manipulated, such as an animal having DNA derived from a different organism, multiple copies of an endogenous gene or having a gene disruption.

As used herein, the term "wild-type animal" refers to an animal having a natural genome without any modifications. Wild-type animals are usually used as control animals in experiments using transgenic varieties of the animal.

BRIEF DESCRIPTION OF THE FIGURES

The instant patent or application file contains at least one drawing executed in color. Copies of the patent or patent application publication with color drawing(s) will be provided by the Office upon request and payment of the necessary fee.

FIGS. 2A-E show the results of experiments evidencing that ND2 is present at the post-synaptic density.

FIG. 5F shows amino acid residues 4-7 of SEQ ID NO:5 (pY)EEI.

FIGS. 6A-C show the results of experiments evidencing that the Src40-49 (SUDAPI-1) peptide specifically interacts with the ND2.1 peptide.

FIGS. 8A-D show results of experiments showing the effects of HIV-TAT on 2.5% formalin induced flinching or biting/licking behaviors.

FIGS. 9A-B show SEQ ID NOS:6 and 7; FIG. 9A shows the nucleotide sequence encoding recombinant ND2.1 protein (SEQ ID NO:6); FIG. 9B shows the amino acid sequence of recombinant ND2.1 protein (SEQ ID NO:7).

FIGS. 14A-D show data illustrating the increase in tyrosine phosphorylation of the NR2B subunit after formalin injection (inflammatory pain model) and further show that this increase of NR2B tyrosine phosphorylation is significantly reduced by intrathecal administration of Src40-49Tat (SEQ ID NO:2).

FIGS. 15A-B show data illustrating the increase in tyrosine phosphorylation of the NR2B in animals having a cuff implant (neuropathic pain model) and further show that this increase of NR2B tyrosine phosphorylation is significantly reduced by intrathecal administration of Src40-49Tat (SEQ ID NO:2).

DETAILED DESCRIPTION OF THE INVENTION

EXAMPLE 1

Figure 1:
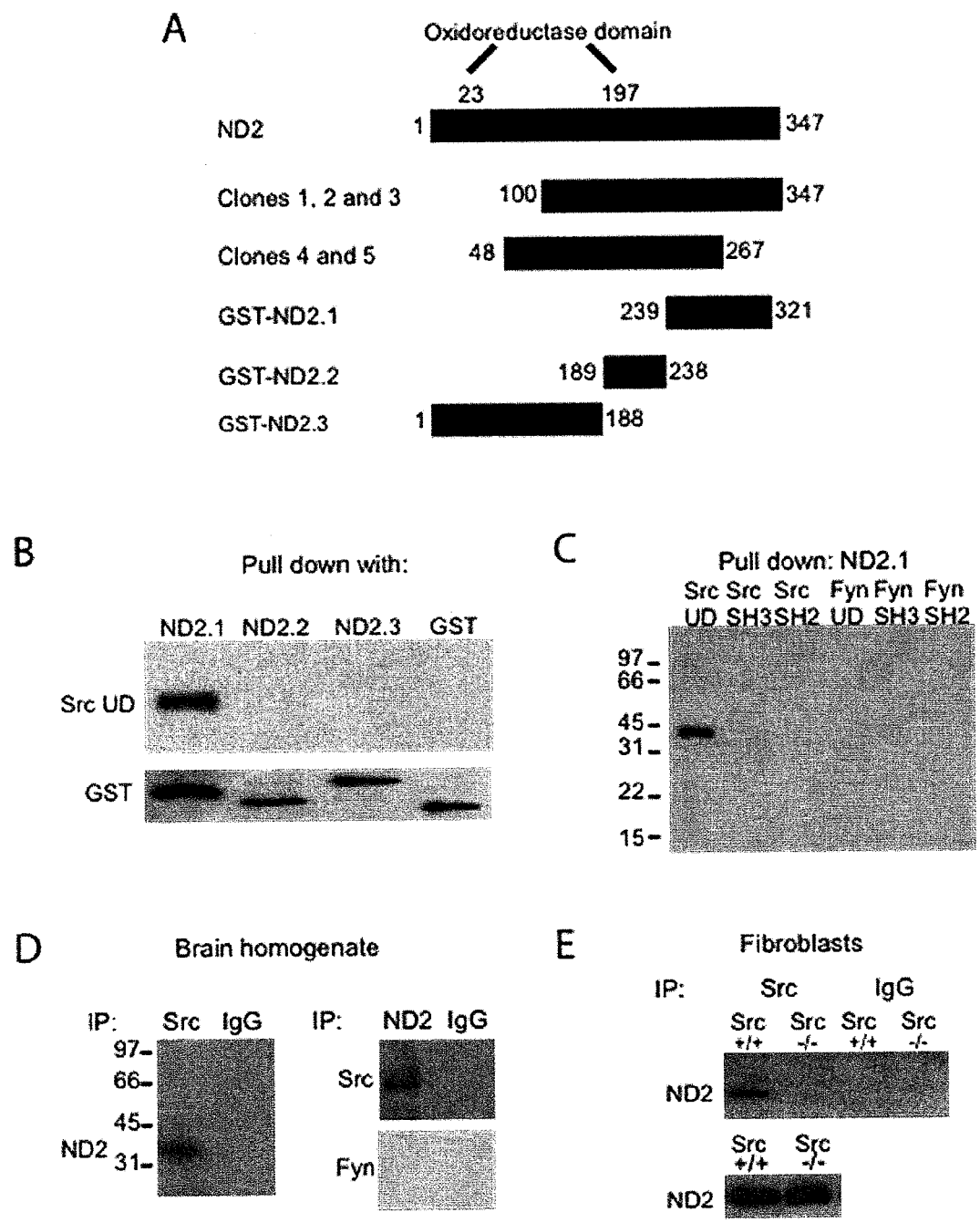
FIGS. 1A-E show the results of experiments evidencing that ND2 is a Src unique domain-interacting protein.

NADH dehydrogenase subunit 2 (ND2) is a Src unique domain-binding protein.

A yeast two-hybrid screen of a fetal brain library using bait constructs containing the murine Src unique domain was conducted in order to search for proteins that interact with the Src unique domain.

cDNAs encoding amino acids 4-82 (the Src unique domain) and amino acids 4-150 (the Src unique and SH3 domains) of murine n-Src were ligated into pEG202 (Gyuris et al. Cell 75:791-803 1993) to create two expression vectors encoding in frame LexA fusions containing the Src unique domain (the nucleotide sequence encoding Src is SEQ ID NO:3 and the amino acid sequence is SEQ ID NO:4). The bait constructs were then sequenced. Both baits were tested to ensure that the baits did not activate transcription of the reporters in the absence of prey and that both could enter the nucleus and bind to LexA operators. To create the selection strains for screening, each bait plasmid was individually transformed into the yeast strain EGY48. EGY48 has an integrated Leu2 selectable marker regulated by 6 LexA operator repeats, and carries a reporter plasmid with the lacZ gene regulated by 8 LexA operator repeats. Bait-prey interactions that occur with low affinity result in activation of the Leu2 reporter gene only, whereas high affinity interactions result in activation of both the Leu2 and lacZ reporter genes, allowing for double selection of prey. The selection strain was transformed with a representative activation-tagged cDNA prey fusion library constructed using ~1 kilobase EcoRI fragmented poly A(+) RNA from human fetal brain. Yeast transformed with the prey library (approximately $1.1 \times 10^6$ clones) were screened by double selection on X-gal Leu⁻ medium. Prey cDNAs encoding proteins that interacted with the bait were isolated and sequenced.

Src, Fyn, and ND2 recombinant proteins were prepared. The cDNAs encoding the SH3 and SH2 domains of mouse n-Src and Fyn were PCR subcloned, ligated in frame into pGEX4T-1 (Amersham Pharmacia Biotech, Baie d'Urfé, Québec), and sequenced. These plasmids, as well as plasmids encoding the unique domains of Src and Fyn in pGEX2T'6, were transformed into BL21 bacteria, and GST fusion proteins were purified by glutathione affinity chromatography. To create the ND2.1, ND2.2, and ND2.3 GST fusion proteins, cDNAs encoding amino acids 239-321 (ND2.1-GST; SEQ ID NO:7), amino acids 189-238 (ND2.2-GST; SEQ ID NO:11), and amino acids 1-188 (ND2.3-GST; SEQ ID NO:13) of human ND2 were PCR subcloned and ligated into pGEX4T-1 (the nucleotide sequence encoding ND2 is SEQ ID NO:8 and the amino acid sequence is SEQ ID NO:9; the nucleotide sequences encoding ND2.1; ND2.2 and ND2.3 are SEQ ID NOS:6, 10 and 12, respectively). Using PCR-based single nucleotide mutagenesis, all cDNAs encoding ND2 fusion proteins were corrected for differences between mitochondrial and nuclear codons to prevent premature translation termination and protein truncation. All constructs were then confirmed by sequencing. The plasmids were transformed into bacteria, and GST fusion proteins were purified by glutathione affinity chromatography.

Detailed protocols for in vitro binding assays, pull down assays, immunoblotting, and co-immunoprecipitation techniques can be found in Pelkey et al. (Neuron 34:127-138 2002).

In two independent screens, cDNA fragments encoding overlapping regions within NADH dehydrogenase subunit 2 (ND2) were isolated (FIG. 1A). ND2 is a 347 amino acid protein (SEQ ID NO:9) that is a subunit of the inner mitochondrial membrane enzyme, NADH dehydrogenase (Complex I). ND2 is one of a group of seven oxidoreductase proteins that are encoded in the mitochondrial genome and which co-assemble with 35 nuclear encoded subunits to form Complex I. ND2 on its own lacks enzymatic activity (J.E. Walker Quarterly Reviews of Biophysics 25(3):253-324 1992; Sazanov et al. Journal of Molecular Biology 302:455-464 2000; Sazanov et al. Biochemistry 39:7229-7235 2000). FIG. 1A is a schematic diagram illustrating the domain structure of ND2, clones isolated from the yeast two hybrid screen, and recombinant GST-tagged fusion proteins. The lines point out the beginning of the oxidoreductase domain at amino acid position 23 and the end at amino acid position 197. Each clone and GST-fusion protein represent overlapping regions within ND2.

As yeast two-hybrid screening may reveal false positive protein-protein interactions, the interaction between Src and ND2 was observed using an independent methodological approach. Direct binding in vitro between ND2 and Src was tested using recombinant proteins. A series of GST fusion proteins comprised of portions of ND2 that spanned the overlapping region found with the yeast two-hybrid screen were made (FIG. 1A). Importantly, the cDNAs encoding each of the ND2 fusion proteins were corrected for differences between mitochondrial and nuclear codons so that the sequence of the ND2 portion of the fusion proteins was that which would have been produced by translation in the mitochondria. For example, FIG. 9A shows the nucleotide sequence encoding recombinant ND2.1 protein (SEQ ID NO:6). Codons that are highlighted with bold type were altered by PCR-based single nucleotide mutagenesis. TGA was changed to TGG to prevent premature translation termination and protein truncation. GAA was changed to GAG to remove a restriction enzyme site. Numbers in parenthesis correspond to equivalent positions in the endogenous human ND2 nucleotide sequence. FIG. 9B shows the amino acid sequence of recombinant ND2.1 protein (SEQ ID NO:7). Numbers in parenthesis correspond to equivalent positions in the endogenous human ND2 amino acid sequence. Each of the series of GST-fusion proteins was tested individually for interaction with the Src unique domain ("pull-down" assay). FIG. 1B shows a blot of ND2-GST fusion proteins probed with biotinylated Src unique domain followed by a streptavidin-HRP conjugate. A GST fusion protein containing amino acids 239-321 of ND2 (ND2.1-GST; SEQ ID NO:7) was found that bound to the unique domain of Src (FIG. 1B). In contrast, GST fusion proteins containing amino acids 189-238 (ND2.2-GST) or 1-188 (ND2.3-GST) of ND2 (ND2 protein sequence is SEQ ID NO:9) did not bind to the Src unique domain. These results, together with those from the yeast two-hybrid screen, indicate that ND2 is a Src unique domain-binding protein. The results indicate further that the Src-binding portion of ND2 is contained within the region of amino acids 239-321 (SEQ ID NO:7). This region of ND2 shows little conservation amongst the mitochondrially encoded oxidoreductase proteins and is outside the so-called "oxidoreductase domain", a signature region identified in all mitochondrially encoded subunits of NADH dehydrogenase (J.E. Walker Quarterly Reviews of Biophysics 25(3):253-324 1992; Sazanov et al. Journal of Molecular Biology 302:455-464 2000; Sazanov et al. Biochemistry 39:7229-7235 2000) and some antiporters (Fearnley et al. Biochim. Biophys. Acta 1140:105-143 1992).

Another "pull-down" assay was conducted to determine whether the binding of ND2 might generalize to other domains of Src or to other Src family tyrosine kinases.

However, it was found that ND2.1-GST did not bind to either of the prototypic protein-protein interaction domains of Src, the SH2 or SH3 domains (FIG. 1C). FIG. 1C shows a blot of ND2.1-GST probed with biotinylated domains of Src and Fyn followed by streptavidin-HRP conjugate.

To examine the potential interaction of ND2 with other kinases of the Src family recombinant domains of Fyn were tested, the protein most closely related to Src but which has little primary sequence conservation in the unique domain (Brown et al. Biochim. Biophys. Acta 1287:121-149 1996; T. Pawson Nature 373:573-580 1995). It was found that ND2.1-GST did not interact in vitro with the Fyn unique domain; nor did ND2.1 bind to the SH2 or SH3 domains of Fyn. Thus, the ND2.1 region does not interact with the SH2 or SH3 domains of Src or Fyn nor does it generally bind to the unique domain of Src family tyrosine kinases.

To investigate the possibility that Src and ND2 may interact in vivo, brain lysates were immunoprecipitated with antibodies directed against ND2 (anti-ND2) or against Src (anti-Src). It was found that immunoprecipitating Src led to co-immunoprecipitation of ND2 (FIG. 1D). FIG. 1D shows immunoblots of co-immunoprecipitates from brain homogenate probed with anti-ND2, anti-Src or anti-Fyn as indicated. Non-specific IgG was used as a negative control for immunoprecipitation. Fyn was readily detected in the brain homogenate used as a starting material for the co-immunoprecipitation (data not illustrated). Conversely, immunoprecipitating with anti-ND2 resulted in co-immunoprecipitation of Src. In contrast, anti-ND2 did not co-immunoprecipitate Fyn and neither ND2 nor Src was immunoprecipitated with a non-specific IgG (FIG. 1D). As an independent immunoprecipitation control it was found that ND2 was co-immunoprecipitated by anti-Src from Src$^{+/+}$ fibroblasts but not from Src$^{-/-}$ fibroblasts (FIG. 1E). FIG. 1E shows an immunoblot of co-immunoprecipitates from cultured Src$^{+/+}$ and Src$^{-/-}$ fibroblasts probed with anti-ND2. Non-specific IgG was used as a negative control for immunoprecipitation, and immunoblotting of ND2 protein from both cell lines was used as a positive control. Thus, in addition to finding the ND2-Src unique domain interaction in two yeast two-hybrid screens and in vitro binding assays with recombinant proteins, it was found that ND2 and Src co-immunoprecipitated with each other, which together led to the conclusion that the ND2 is a Src unique-domain binding protein that may interact with Src in vivo.

EXAMPLE 2

ND2 is present in post-synaptic densities in brain.

Post-synaptic density proteins (Kennedy et al. Proceedings of the National Academy of Science USA 80:7357-7361 1983) were prepared from rat brain as described in detail (Pelkey et al. Neuron 34:127-138 2002). Cellular fractionation of rat brain tissue into nuclear, heavy mitochondrial, light mitochondrial, microsomal, and cytosolic fractions was performed by differential centrifugation of tissue homogenate in 0.25 M sucrose/10 mM HEPES-NaOH, 1 mM EDTA, pH 7.4 with 2 μg each of aprotinin, pepstatin A, and leupeptin (Sigma, St. Louis, Mo.) at 4° C. Nuclei were pelleted by centrifugation at 1 000 g for 10 minutes, the supernatant was removed and spun at 3 000 g for 10 minutes to obtain a heavy mitochondrial pellet. The supernatant was removed and spun at 16 000 g for 15 minutes to obtain a light mitochondrial pellet. The supernatant was removed and spun at 100 000 g for 1 hour to obtain a microsomal pellet and the cytosolic fraction. All pellets were then resuspended in RIPA buffer (50 mM Tris pH 7.6, 150 mM NaCl, 1 mM EDTA, 1% NP-40, 2.5 mg/ml NaDOC, 1 mM Na$_3$VO$_4$ 1 mM PMSF, and 2 μg/ml each of protease inhibitors). The light mitochondrial fraction was used in subsequent experiments. For Western blots, 50 μg of total protein was loaded per lane, resolved by SDS-PAGE, transferred to nitrocellulose membranes, and probed with anti-ND2, anti-Cyto1 and anti-ND4 (mouse monoclonals, Molecular Probes Inc., Eugene, Oreg.), anti-PSD95 (mouse monoclonal clone 7E3-1B8, Oncogene Research Products, Cambridge, Mass.), anti-NR1 (mouse monoclonal clone 54.1, Pharmingen), anti-Src, or anti-synaptophysin (mouse monoclonal, Sigma).

Post-embedding immunogold electron microscopy was carried out. Sprague Dawley rats were anesthetized and perfused with 4% paraformaldehyde plus 0.5% glutaraldehyde in 0.1 M phosphate buffer. Parasagittal sections of the hippocampus were cryoprotected in 30% glycerol and frozen in liquid propane. Frozen sections were immersed in 1.5% uranyl acetate in methanol at −90° C., infiltrated with Lowicryl HM-20 resin at −45° C., and polymerized with ultraviolet light. Sections were incubated in 0.1% sodium borohydride plus 50 mM glycine in TBS and 0.1% Triton X-100 (TBST), followed by 10% normal goat serum (NGS) in TBST, primary antibody in 1% NGS in TBST, and immunogold (10 nm; Amersham Pharmacia Biotech) in 1% NGS in TBST plus 0.5% polyethylene glycol. Finally, the sections were stained in uranyl acetate and lead citrate prior to analysis.

Figure 16:
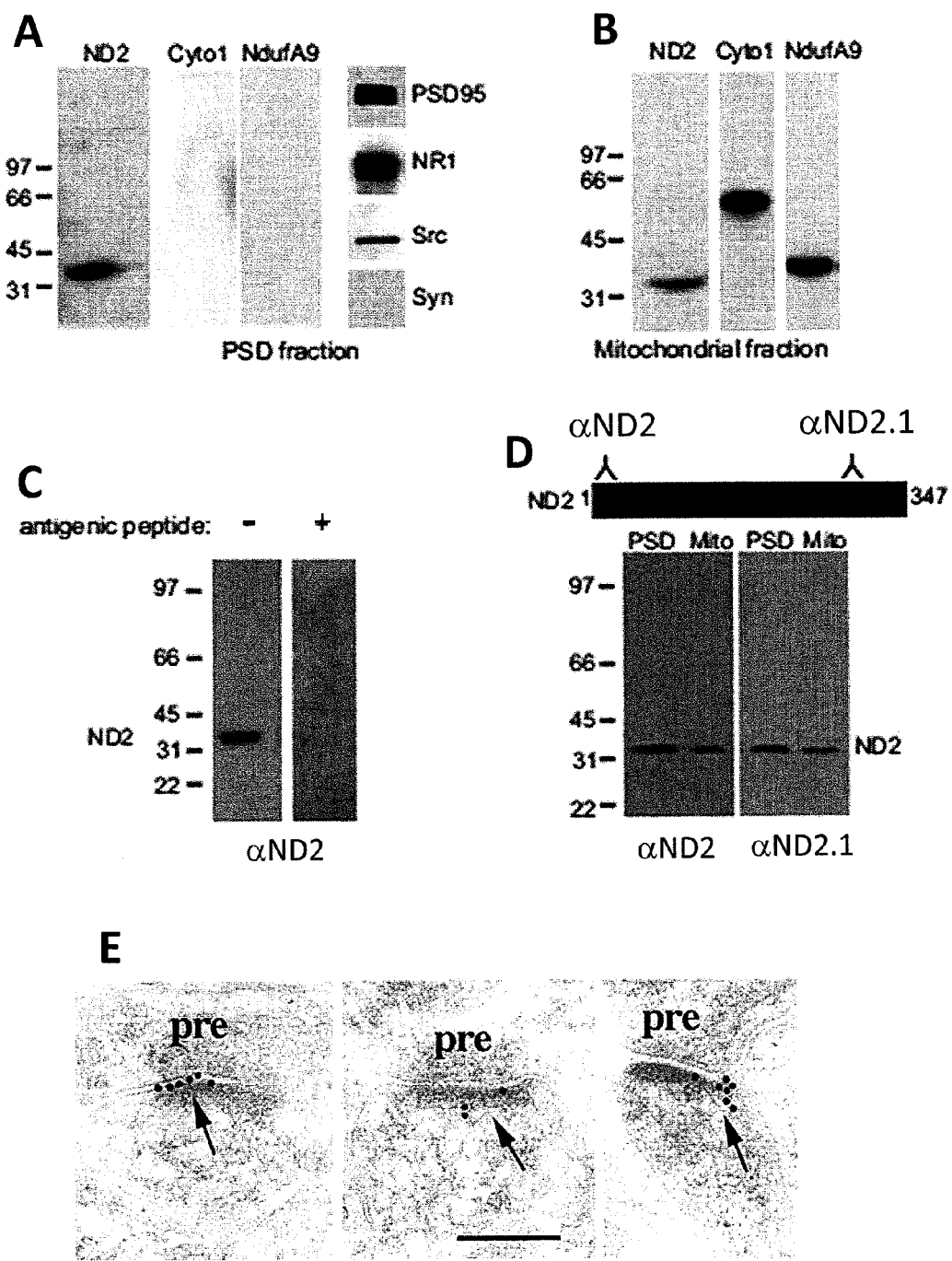
FIGS. 16A-E show the results of experiments evidencing that an antibody against ND2 recognizes NADH-Ubiquinone Oxidoreductase 1 alpha subcomplex 9 (NdufA9), a subunit of mitochondrial complex I (NCBI GeneID:4704).

In the CNS a prominent subcellular location for Src is in the post-synaptic density (PSD) (Yu et al. Science 275:674-678 1997), a subsynaptic specialization at glutamatergic synapses comprised of α-amino-3-hydroxy-5-methylisoxazolepropionic acid (AMPA-) and NMDA-type glutamate receptors together with scaffolding, signaling and regulatory proteins (Walikonis et al. Journal of Neuroscience 20:4069-4080 2000). Because Src is known to regulate subsynaptic NMDARs (Yu et al. Science 275:674-678 1997), if ND2 is the protein mediating the interaction between NMDARs and the unique domain of Src then ND2 is predicted to be present in the PSD. This was tested by preparing PSD proteins from rat brain homogenates by sequential fractionation and determining whether ND2 was present in this fraction. Characteristic of a bona fide PSD fraction, the fraction which was prepared contained post-synaptic proteins including PSD-95 and NMDA receptor subunit proteins but lacked the pre-synaptic protein synaptophysin (FIG. 2A). FIG. 2A shows immunoblots of PSD proteins probed with anti-ND2, anti-cytochrome c oxidase I (Cyto 1), anti-ND4, anti-PSD95, anti-NR1, anti-Src and anti-synaptophysin as indicated. It was found that ND2 was present in the PSD fraction and the amount of ND2 estimated in this fraction was approximately 15% of that in the total brain homogenate. In contrast to ND2, neither the oxidoreductase protein ND4, another mitochondrially-encoded component of Complex I (J. E. Walker Quarterly Reviews of Biophysics 25(3):253-324 1992; Sazanov et al. Journal of Molecular Biology 302:455-464 2000; Sazanov et al. Biochemistry 39:7229-7235 2000) nor cytochrome c oxidase subunit 1 (Cyto 1), an inner mitochondrial membrane protein that is part of Complex IV (Marusich et al. Biochim. Biophys. Acta 1362:145-159 1997), was detectable in the PSD fraction. On the other hand, Cyto 1 and ND4, as well as ND2, were readily detected in proteins from brain mitochondria (FIG. 2B). Subsequent investigation indicated that the NdufA9 (NADH-ubiquinone oxidoreductase 1 alpha subcomplex 9) subunit of mitochondrial complex I was detected and not ND4 (FIG. 16B). FIG. 2B shows immunoblots of mitochondrial proteins prepared by differential centrifugation probed with anti-ND2, anti-Cyto 1 and anti-ND4. Neither NR1 nor NR2A/B was detected in the mitochondrial fraction (data not shown).

As noted above, subsequent investigations indicated that the antibody initially thought to recognize the mitochondrial protein ND4, a control in the study, actually recognizes NADH-Ubiquinone Oxidoreductase 1 alpha subcomplex 9 (NdufA9). Like ND4, NdufA9 protein has a molecular weight of 39 kDa and is a subunit of NADH dehydrogenase (mitochondrial complex I). However, unlike ND4, NdufA9 is encoded in the nucleus. Because NdufA9 is a subunit of mitochondrial complex I, as is ND4, NdufA9 is also an appropriate control for the instantly described experiments (Gingrich et al. PNAS 103(25):9744 2006; published online on Jun. 8, 2006). Referring now to FIGS. 16A-B, characteristic of a bona fide PSD fraction, the fraction which was prepared contained post-synaptic proteins including PSD-95 and NMDA receptor subunit proteins but lacked the pre-synaptic protein synaptophysin (FIG. 16A) FIG. 16A shows immunoblots of PSD proteins probed with anti-ND2, anti-cytochrome c oxidase I (Cyto 1), anti-NdufA9, anti-PSD95, anti-NR1, anti-Src and anti-synaptophysin as indicated. It was found that ND2 was present in the PSD fraction. In contrast to ND2, neither the NADH-Ubiquinone Oxidoreductase 1 alpha subcomplex 9 (NdufA9), a subunit of mitochondrial complex I, nor the cytochrome c oxidase subunit 1 (Cyto 1), an inner mitochondrial membrane protein that is part of Complex IV (Marusich et al. Biochim. Biophys. Acta 1362:145-159 1997), were detectable in the PSD fraction. On the other hand, Cyto 1 and NdufA9, as well as ND2, were readily detected in proteins from brain mitochondria (FIG. 16B). FIG. 16B shows immunoblots of mitochondrial proteins prepared by differential centrifugation probed with anti-ND2, anti-Cyto 1 and anti-NdufA9. FIGS. 16C-E are identical to FIGS. 2C-E.

Although the molecular size of the protein detected by anti-ND2 in the PSD preparation matched that of ND2 in mitochondria, it is conceivable that the protein detected in the PSD preparation was not ND2 but a protein of the same molecular size that was recognized by anti-ND2. However, it was found that incubating anti-ND2 with the antigen to which the antibody was raised prevented the immunoblotting signal (FIG. 2C). FIG. 2C shows immunoblots of PSD proteins showing the specificity of the N-terminal ND2 antibody by pre-adsorption with the antigenic peptide used to derive the antibody. Morever, it was found that a separate antibody directed towards a distinct epitope in a region of ND2 remote from that of the anti-ND2 epitope also detected ND2, at the correct molecular size, in the PSD preparation, as well as in the mitochondrial preparation (FIG. 2D). FIG. 2D shows immunoblots of PSD and mitochondrial proteins probed with two independent rabbit polyclonal antibodies directed against two disparate regions of ND2. The N-terminal ND2 antibody was used for all subsequent experiments illustrated. Thus, ND2 was found in the PSD preparation by two separate antibodies, and this could not be accounted for by a general contamination with mitochondrial proteins because neither Cyto 1 nor ND4 were detected in the PSD.

In addition to examining PSD protein preparations, the presence of ND2 in PSDs was tested for by means of post-embedding immunogold electron microscopy in the CA1 stratum radiatum of rat hippocampus (Petralia et al. Nature Neuroscience 2:31-36 1999; Sans et al. Journal of Neuroscience 20:1260-1271 2000). With this experimental approach the tissue is fixed immediately after the animal is sacrificed and prior to sectioning so that protein localization is preserved. ND2 labeling was found, as visualized by secondary antibody conjugated to 10 nm gold particles, in the PSD and the postsynaptic membrane in dendritic spines of CA1 neurons (FIG. 2E), as well as over mitochondria (not illustrated). FIG. 2E shows three representative post-embedding immunogold electron microscopy images of rat hippocampus CA1 synapses, pre-synaptic. Scale bar is 200 nm. ND2 labeling was enriched in the post-synaptic membrane approximately 30-fold as compared with the plasma membrane in the remainder of the dendritic spine (0.37 particles per PSD/section versus 0.012, $p<0.05$) and there was no obvious accumulation of ND2 labeling along the plasma membrane of the dendritic shaft. The ND2 labeling observed in the PSD and post-synaptic membrane could not have been due to labeling in mitochondria because it is known that mitochondria are excluded from dendritic spines (Shepherd et al. Journal of Neuroscience 18(20):8300-8310 1998). Thus, these results indicate that ND2 is present in the biochemically defined PSD protein fraction and is localized at PSDs in CA1 neurons.

EXAMPLE 3

ND2 interacts with Src at the NMDA receptor complex in post-synaptic densities.

Figure 3:
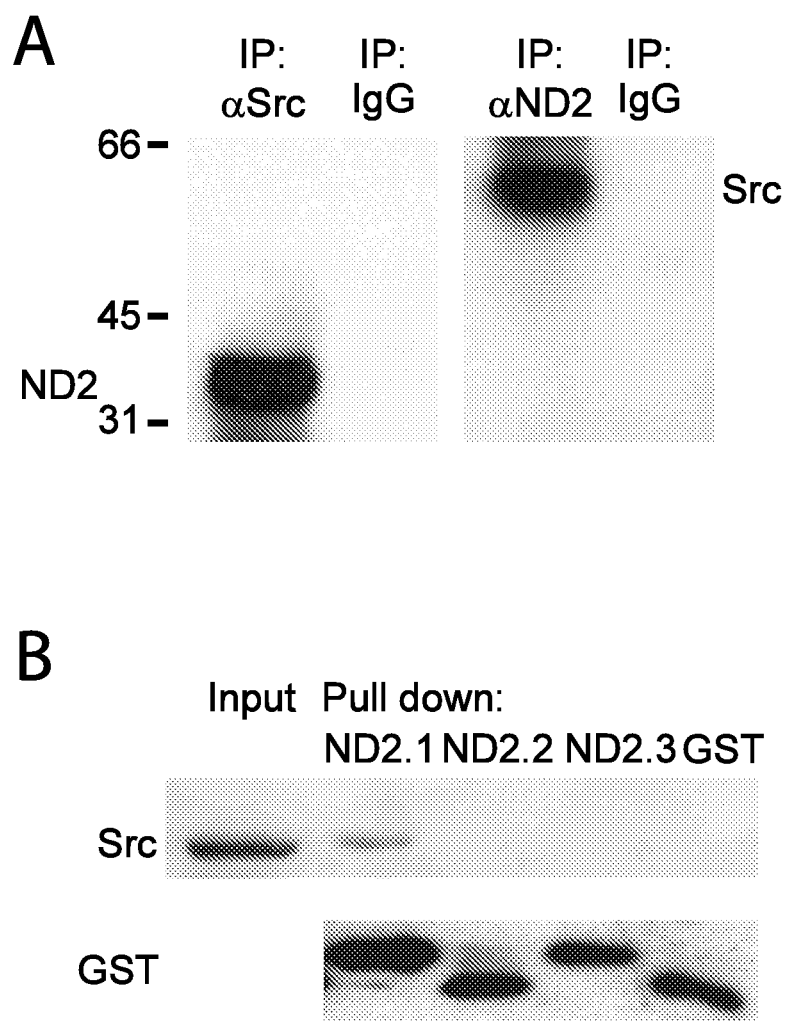
FIGS. 3A-B show the results of experiments evidencing that ND2 interacts with Src at the post-synaptic density.

Since previous results indicate that ND2 is present in PSDs from brain, it was examined whether ND2 interacts with Src in PSDs. It was found that immunoprecipitating ND2 from the PSD fraction led to co-immunoprecipitation of Src and vice versa (FIG. 3A), indicating that ND2 and Src interact post-synaptically at glutamatergic synapses. FIG. 3A shows immunoblots of co-immunoprecipitates from PSD preparations probed with anti-ND2 or anti-Src as indicated. Non-specific IgG (either rabbit or mouse) was used as a negative control for both antibodies. Moreover, Src was pulled from the PSD fraction by the fusion protein ND2.1-GST, but not by either ND2.2- or ND2.3-GST (FIG. 3B). FIG. 3B shows recombinant ND2.1-GST fusion protein, but not ND2.2-GST, ND2.3-GST, or GST alone, pulls Src form PSD preparations. Thus, as it was found with the Src-ND2 binding in vitro, these results indicate that amino acids 239-321 of ND2 (SEQ ID NO:7) are both necessary and sufficient for ND2 to interact with Src in the PSD.

Figure 4:
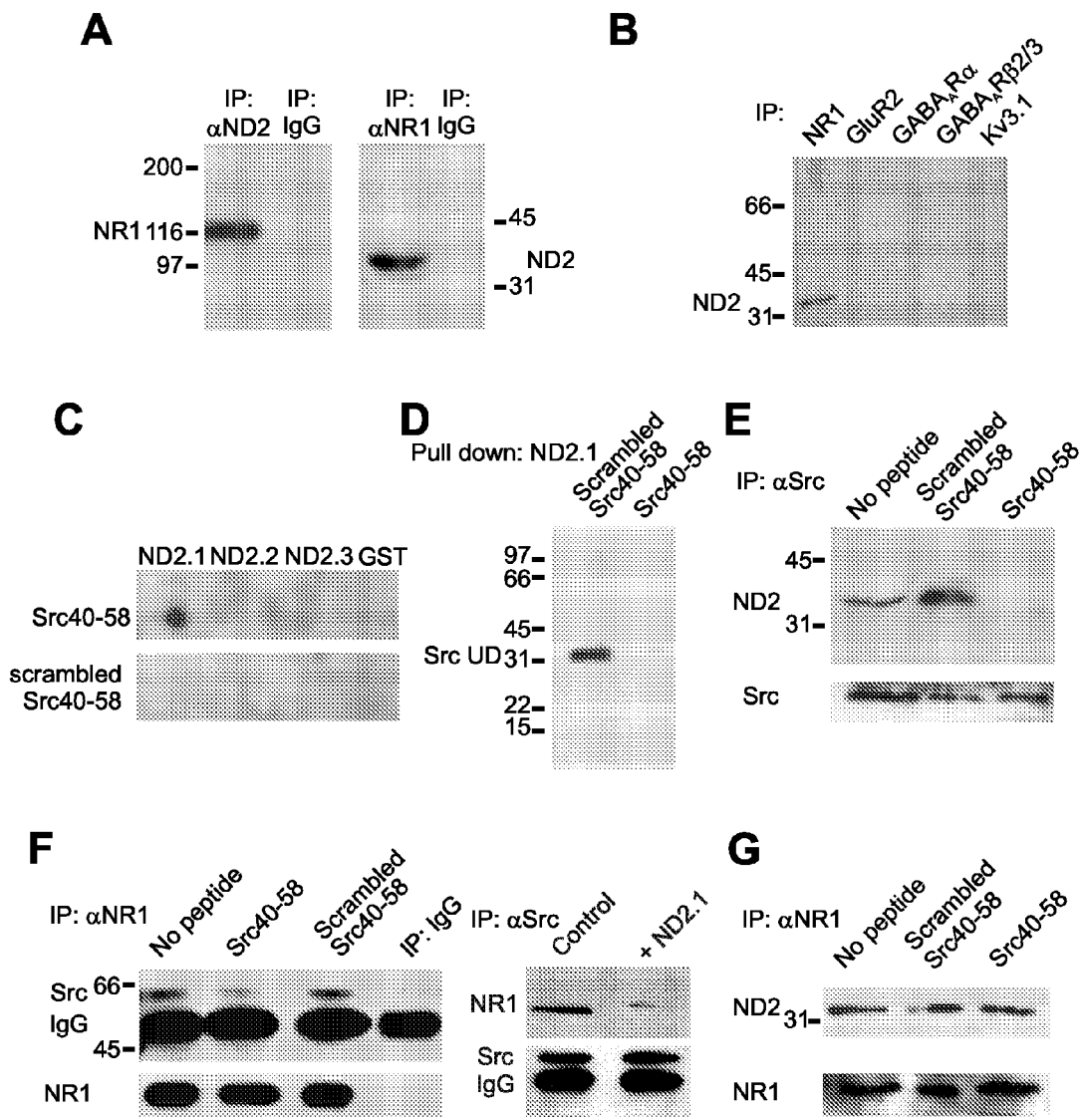
FIGS. 4A-G show the results of experiments evidencing that ND2 interacts with Src at the NMDAR complex.

The hypothesis that ND2 is the protein mediating the interaction between Src and NMDARs requires that, in addition to being present in the PSD and interacting there with Src, ND2 is part of NMDAR complex of proteins. To determine whether ND2 is a component of the NMDAR protein complex, NMDAR complexes were immunoprecipitated from the PSD fraction, using an antibody directed against the core NMDAR subunit NR1 (Dingledine et al. Pharmacology Reviews 51:7-61 1999), and the co-immunoprecipitating proteins were probed with anti-ND2. It was found that ND2 co-immunoprecipitated (FIG. 4A), and conversely, immunoprecipitating with anti-ND2 led to co-immunoprecipitation of NR1 (FIG. 4A). FIG. 4A shows immunoblots of co-immunoprecipitates from PSD preparations probed with anti-ND2 or with anti-NMDA receptor subunit 1 (NR1) as indicated. Non-specific IgG (either rabbit or mouse) was used as a negative control for both antibodies. Neither ND2 nor NR1 was immunoprecipitated by non-specific IgG, and ND2 did not co-immunoprecipitate with the potassium channel Kv3.1

(FIG. 4B), a negative control for non-specific immunoprecipitation of post-synaptic proteins, therefore it was concluded that ND2 is an NMDAR complex protein. FIG. 4B shows an immunoblot of co-immunoprecipitates from PSD preparations using anti-GluR2, anti-GABA$_A$Rα, anti-GABA$_A$Rβ2/3 and anti-Kv3.1 antibodies to immunoprecipitate. Probe was anti-ND2. Importantly, neither ND4 nor Cyto 1 was detected in co-immunoprecipitates of NR1 (not illustrated) indicating that mitochondrial proteins in general are not components of the NMDAR complex. Moreover, ND2 did not co-immunoprecipitate with GluR2, GABA$_A$Rα or GABA$_A$Rβ2/3 (FIG. 4B) indicating that ND2 is not a detectable component of AMPA receptor or γ-aminobutyric acid (GABA) receptor complexes.

Thus, while ND2 is a component of NMDAR complexes it is not generally a component of neurotransmitter receptor complexes in the brain.

EXAMPLE 4

ND2 acts as an adapter protein for Src.

Src40-58 and scrambled Src peptides were biotinylated by incubating with Sulfo-NHS-Biotin (Pierce Chemical Co., Rockford, Ill.) for 30 minutes at room temperature (SEQ ID NO:4, Src protein). The biotinylation reaction was then quenched by the addition of Tris-HCl (pH 8.0) to a final concentration of 20 mM. Purified recombinant fusion proteins (~20 μg each) were dotted onto nitrocellulose and dried overnight. Membranes were blocked with 5% BSA in PBS for 1 hour, after which biotinylated peptides (30 μg/ml) diluted 1:1000 in fresh 5% BSA in PBS were added. The membranes were incubated with the peptides for 1 hour, washed, and probed using a streptavidin-HRP conjugate. Bound probe was then detected on film using an ECL kit.

ND2 acts as an adapter protein for Src. Amino acids 40-58 (SEQ ID NO:4) within the Src unique domain have been implicated in the binding of Src to the interacting protein in the NMDAR complex (Yu et al. Science 275:674-678 1997; Lu et al. Science 279:1363-1368 1998; Yu et al. Nature 396: 469-474 1998) and thus, ND2 was predicted to bind to this region of Src. This prediction was examined in vitro using a peptide with the sequence of amino acids 40-58 (Src40-58; SEQ ID NO:4) which was found to bind directly to ND2.1-GST (FIG. 4C) in vitro. In contrast, a peptide with identical amino acid composition, but a scrambled sequence (scrambled Src40-58), did not bind to ND2.1-GST. Neither Src40-58 nor scrambled Src40-58 bound to ND2.2-GST, ND2.3-GST or to GST alone (FIG. 4C). FIG. 4C shows a dot blot of ND2-GST fusion proteins probed with biotinylated Src40-58 or scrambled Src40-58 peptides followed by streptavidin-HRP conjugate. Furthermore, the effect of Src40-58 on the interaction between Src and ND2 was examined (FIGS. 4D and 4E). It was found that incubating ND2.1-GST with Src40-58 prevented this fusion protein from pulling down the Src unique domain protein in vitro (FIG. 4D). FIG. 4D shows a blot of ND2.1-GST probed with boptinylated Src unique domain in the presence of either Src40-58 or scrambled Src40-58 peptides followed by streptavidin-HRP conjugate. On the other hand, scrambled Src40-58 did not affect the interaction between the ND2.1-GST and Src unique domain proteins. Incubating PSD proteins with Src40-58 prevented the co-immunoprecipitation of ND2 by anti-Src but this was not affected by scrambled Src40-58 (FIG. 4E). FIG. 4E shows immunoblots of co-immunoprecipitates obtained from PSD proteins in the presence of either Src40-58 or scrambled Src40-58 probed with anti-ND2 or stripped and re-probed with anti-Src. Importantly, Src40-58 did not affect the immunoprecipitation of Src from PSDs. Thus, it was concluded that amino acids 40-58 of Src interact with the region spanned by ND2.1, thereby mediating the binding between the Src unique domain and ND2.

As ND2 alone is not catalytically active (J. E. Walker Quarterly Reviews of Biophysics 25(3):253-324 1992; Sazanov et al. Journal of Molecular Biology 302:455-464 2000; Sazanove et al. Biochemistry 39:7229-7235 2000), its functional role in the NMDAR complex was investigated. ND2 might be a phosphorylation target for Src, but it was found that ND2 immunoprecipitated from PSD protein fractions was not detectably phosphorylated on tyrosine. Moreover, inclusion of ND2.1-GST did not alter the catalytic activity of Src in vitro (not illustrated) consistent with the binding of ND2 to the unique domain rather than to the regulatory or catalytic domains. Thus, it is unlikely that ND2 is a target of Src or a regulator of Src kinase activity.

However, it was found that the co-immunoprecipitation of Src with NMDARs (FIG. 4F, left panel) was suppressed by Src40-58, but not scrambled Src40-58, and by ND2.1 (FIG. 4F, right panel) indicating that the association of Src with the NMDAR complexes depends on the interaction with ND2. FIG. 4F, left panel shows immunoblots of co-immunoprecipitates obtained from PSD proteins in the presence of either Src40-58 or scrambled Src40-58. FIG. 4F, right panel shows immunoblots of co-immunoprecipitates obtained from PSD proteins in the presence of GST-ND2.1 fusion protein probed with anti-Src or anti-NR1 as indicated. In contrast, the co-immunoprecipitation of ND2 with NMDARs was not affected by Src40-58 (FIG. 4G), implying that binding ND2 to Src is not necessary for ND2 to associate with NMDAR complexes. FIG. 4G shows immunoblots of co-immunoprecipitates obtained from PSD proteins in the presence of either Src40-58 or scrambled Src40-58 peptides preobed with anti-ND2 or stripped and re-probed with anti-NR1. Taking these results together, it was concluded that ND2 may function as an adapter protein that anchors Src in the NMDAR complex.

EXAMPLE 5

Loss of ND2 in neurons prevents the regulation of NMDA receptor activity by Src.

Fetal rat hippocampal neurons were prepared, cultured, and used for electrophysiological recordings 12-17 days after plating. Methods for whole cell recordings are described in Pelkey et al. (Neuron 34:127-138 2002).

Figure 5:
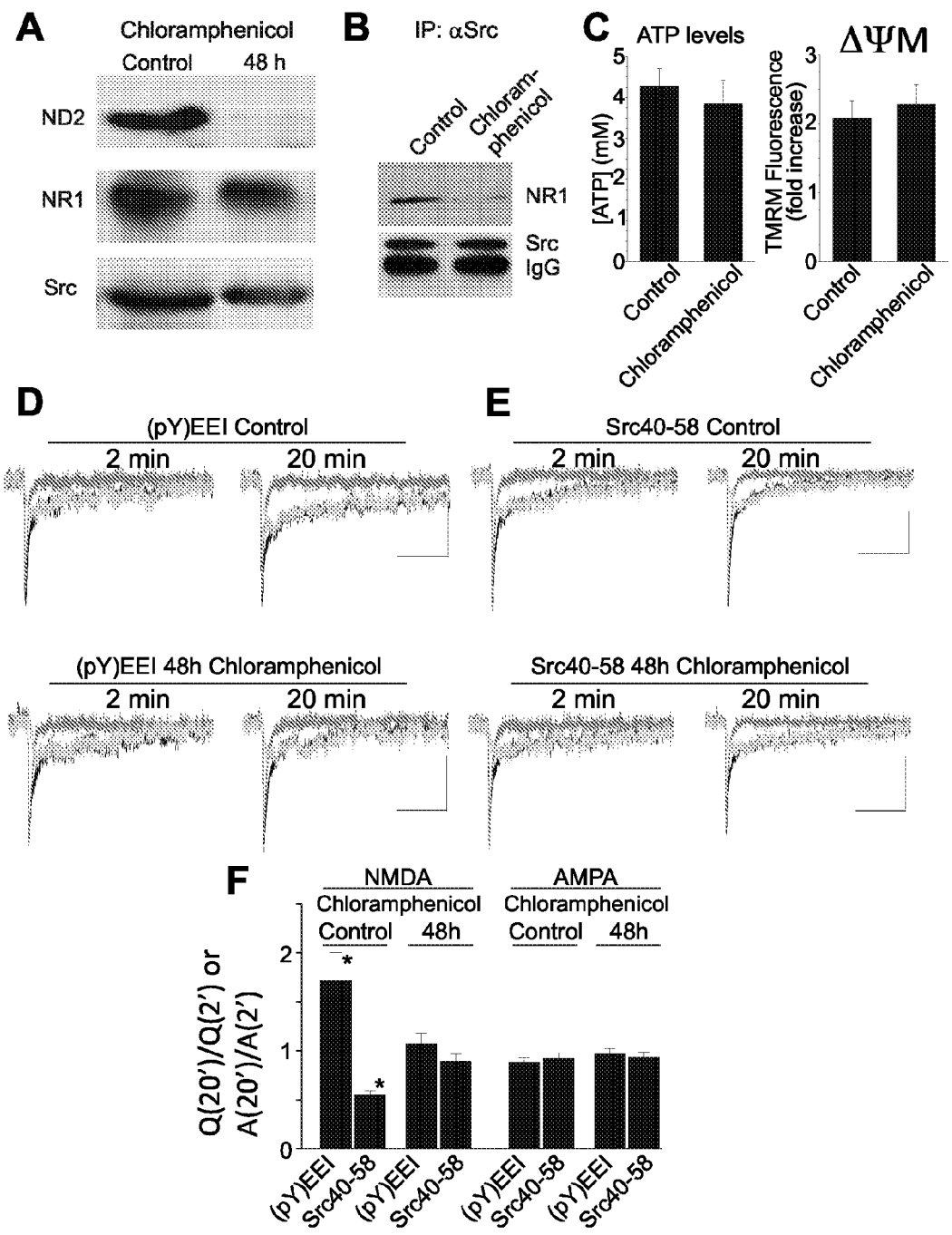
FIGS. 5A-F show the results of experiments evidencing that blocking expression of ND2 prevents Src-dependent regulation of NMDA receptor activity.

It was hypothesized that if ND2 is a Src adapter protein then loss of ND2 should prevent the upregulation of NMDAR activity by endogenous Src (Yu et al. Science 275:674-678 1997). This was tested by investigating miniature excitatory post-synaptic currents (mEPSCs) recorded from cultured hippocampal neurons (MacDonald et al. Journal of Physiology (London) 414:17-34 1989). In these neurons the NMDAR-mediated component of mEPSCs is increased by activating endogenous Src with a high-affinity activating phosphopeptide EPQ(pY)EEIPIA (Liu et al. Oncogene 8:1119-1126 1993) and is reduced by applying Src40-58 (Yu et al. Science 275:674-678 1997). It is predicted that each of these effects will be lost by blocking the expression of ND2, if it acts as an adapter protein for Src in the NMDAR complex. In order to suppress ND2 expression, the hippocampal cultures were treated with chloramphenicol to selectively inhibit translation of mitochondrially encoded proteins but not translation of proteins encoded in the nucleus (Ibrahim et al. Journal of Biological Chemistry 251:108-115 1976). After 48 hours treatment with chloramphenicol it was found that the level of ND2 in the cultures was reduced by more than 95% whereas there was no significant change in the levels of the nuclear encoded proteins examined (FIG. 5A). FIG. 5A shows immunoblots of total soluble protein obtained from cultured rat hippocampal neurons treated with 50 µg/ml chloramphenicol for 48 hours and probed with anti-ND2, anti-NR1 and anti-Src as indicated. Importantly, chloramphenicol did not affect the level of Src or of the NMDAR subunit NR1 but did suppress the co-immunoprecipitation of Src with the NMDAR complex (FIG. 5B), as predicted if ND2 is an adapter protein linking Src to the complex. FIG. 5B shows an immunoblot of co-immunoprecipitates obtained from cultured hippocampal neurons, either treated or untreated with 50 µg/ml chloramphenicol for 48 hours and probed with anti-NR1 or anti-Src.

The effect of the 48 hours treatment with chloramphenicol on the ATP levels, mitochondrial membrane potential, viability and general functioning of the hippocampal neurons in culture was examined. It was found that chloramphenicol did not significantly affect the level of ATP levels in the cultures (FIG. 5C), consistent with the lack of effect of chloramphenicol treatment for up to 55 hours on ATP levels in other cell types in culture (Ramachandran et al. Proceedings of the National Academy of Science USA 99:6643-6648 2002). FIG. 5C shows summary histograms (left panel) of ATP level or mitochondrial membrane potential ($\Delta\psi M$), as assessed by TMRM fluorescence dequenching (right panel), in cultured hippocampal neurons either untreated or treated 50 µg/ml chloramphenicol for 48 hours. To examine the effect of chloramphenicol on mitochondrial membrane potential ($\Delta\psi M$) in individual neurons, the dequenching of the potentiometric fluorescent cationic dye tetramethylrhodamine methyl ester (TMRM) by the mitochondrial uncoupler carbonyl cyanide p-trifluoromethoxyphenylhydrazone (FCCP) was monitored (Reers et al. Biochemistry 30:4480-4486 1991). The dequenching response evoked by bath-applied FCCP (2 µM) in neurons from chloramphenicol-treated or control cultures was assessed. It was found that the dequenching response of chloramphenicol-treated neurons was not different from that of untreated neurons (FIG. 5C), indicating that $\Delta\psi M$ was not affected by chloramphenicol. Moreover, it was found that neurons treated with chloramphenicol were not distinguishable from untreated neurons in terms of cell number, gross morphology, resting membrane potential, resting intracellular calcium concentration, action potential amplitude, or mEPSC frequency (data not illustrated). Thus, from these data together it was concluded that treatment with chloramphenicol for 48 hours did not detectably compromise the functioning of the neurons. Nevertheless, it was noted that the intracellular solution used for all whole-cell recordings contained 2 mM Mg-ATP, so that the level of intracellular ATP was equal in all cells throughout the experiments.

In neurons treated with chloramphenicol for 48 hours it was found that the NMDAR component of the mEPSCs was not affected by administering either the EPQ(pY)EEIPIA (SEQ ID NO:5) peptide or the Src40-58 peptide (FIGS. 5D-F). In contrast, in control experiments administering EPQ (pY)EEIPIA (SEQ ID NO:5) increased the NMDAR component of mEPSCs by 172±28% and application of Src40-58 decreased the NMDAR component to 56±4% (FIGS. 5D-F). Chloramphenicol was present during the recording periods of the control experiments and therefore the loss of effect of the EPQ(pY)EEIPIA (SEQ ID NO:5) and Src40-58 peptides cannot be attributed to an acute effect of chloramphenicol. FIG. 5D shows that the upregulation of NMDAR activity in the presence of the Src activator peptide EPQ(pY)EEIPIA (SEQ ID NO:5), labeled as (pY)EEI (amino acid residues 4-7 of SEQ ID NO:5), is prevented in neurons treated with chloramphenicol for 48 hours. FIG. 5E shows that the reduction of NMDA activity in the presence of the Src40-58 peptide is also prevented in neurons treated with chloramphenicol for 48 hours. Composite traces are shown in black, the NMDAR component in dark grey, and the AMPAR component in light grey. Scale bars are 50 ms/10 pA. FIG. 5F shows a summary histogram of electrophysiology data. NMDA component data were calculated as $Q_{20'}/Q_{2'}$, and AMPA component data were calculated as $A_{20'}/A_{2'}$. A 48 hour chloramphenicol treatment prevents the modulation of NMDAR function by the Src activator peptide (SEQ ID NO:5) and Src40-58 peptides, while neither of these reagents affected the AMPA receptor component of the MEPSCs under the recording conditions used. An * indicates a significant difference, Student's t-test, p<0.05. Taking our results together, it is concluded that Src-dependent regulation of the activity of NMDARs depends on expression of ND2 through its anchoring of Src to the NMDAR complex.

EXAMPLE 6

Src40-49 interacts directly with ND2

To detect the binding of ND2.1-GST with Src peptides, the ND2.1-GST fusion protein was purified on glutathione SEPHAROSE. Src40-58, Src40-49, Src49-58, and scrambled Src40-58 peptides (30 mg/ml; synthesized by HSC Peptide Synthesis Facility; all four peptides are schematically depicted in FIG. 6A) were biotinylated by incubating with Sulfo-NHS-Biotin (Pierce Chemical Co., Rockford, Ill.) for 30 minutes at room temperature. The biotinylation reaction was then quenched by the addition of Tris-HCl (pH 8.0) to a final concentration of 20 mM. Biotinylated peptides were incubated with ND2.1-GST on beads for 1 hour at 4° C. The beads were washed three times with PBS/0.1% Triton X-100, then resuspended in PBS+SDS-PAGE sample buffer. After brief centrifugation, samples were resolved by SDS-PAGE, transferred to nitrocellulose membranes, and probed using a streptavidin-HRP conjugate (Sigma, St. Louis, Mo.). Bound probe was then detected on film using an ECL kit (Amersham Pharmacia Biotech, Baie d'Urfé, Québec). FIG. 6B shows the blot of the ND2.1-GST fusion protein which was probed with biotinylated Src peptides followed by streptavidin-HRP conjugate.

Src40-58, Src40-49, Src49-58, scrambled Src40-58, TAT-Src40-49, and scrambled TAT-Src40-49 peptides were biotinylated by incubating with Sulfo-NHS-Biotin (Pierce Chemical Co., Rockford, Ill.) for 30 minutes at room temperature. The biotinylation reaction was then quenched by the addition of Tris-HCl (pH 8.0) to a final concentration of 20 mM. Purified recombinant fusion proteins (~20 µg each) were dotted onto nitrocellulose and dried overnight. Membranes were blocked with 5% BSA in PBS (pH 7.5) for 1 hour, after which biotinylated peptides (30 µg/ml) diluted 1:1000 in fresh 5% BSA in PBS were added. The membranes were incubated with the peptides for 1 hour, washed, and probed with streptavidin-HRP conjugate. Bound probe was then detected on film using an ECL kit. FIG. 6C shows the dot blots of ND2.1-GST fusion proteins probed with biotinylated Src peptides followed by streptavidin-HRP conjugate.

EXAMPLE 7

TAT-Src40-49 (TSUDAPI-1) reduces pain behavior

Male Sprague-Dawley rats 150-200 g were used for all experiments. Rats were housed in pairs, maintained on a 12/12 hour light/dark cycle, and allowed free access to food and water. All experiments were conducted during 10 am and 5 pm.

Peptide Src40-49Tat (TSUDAPI-1; SEQ ID NO:2) or Tat alone (amino acid residues 1-11 of SEQ ID NO:2) was dissolved in sterilized saline. Peptide or saline was injected intravenously at a volume 1 ml/Kg into rat's tail 45 minutes before behavioral testing. Injections were done under brief halothane anesthesia and rats were returned to the cages after injections.

The formalin test was performed as previously described (Liu et al. European Journal of Pharmacology 408(2):143-152 2000). Rats were placed in a plexiglass observation chamber for an initial 20 minutes to allow acclimatization to the testing environment. Formalin 2.5% was injected subcutaneously in a volume of 50 ml into the plantar aspect of the hind paw. Following injections, rats were returned to the observation chamber and monitored for flinching behaviors (lifting, shaking and overt flinching with a ripple over the haunch) and biting/licking time. Two rats in adjacent chambers were observed at one time, with observations occurring in alternate 2 minute bins. Recorded episodes were not corrected, thus values represent about half of the total behaviors expressed.

Figures 7A, 7B, 7C, 7D:
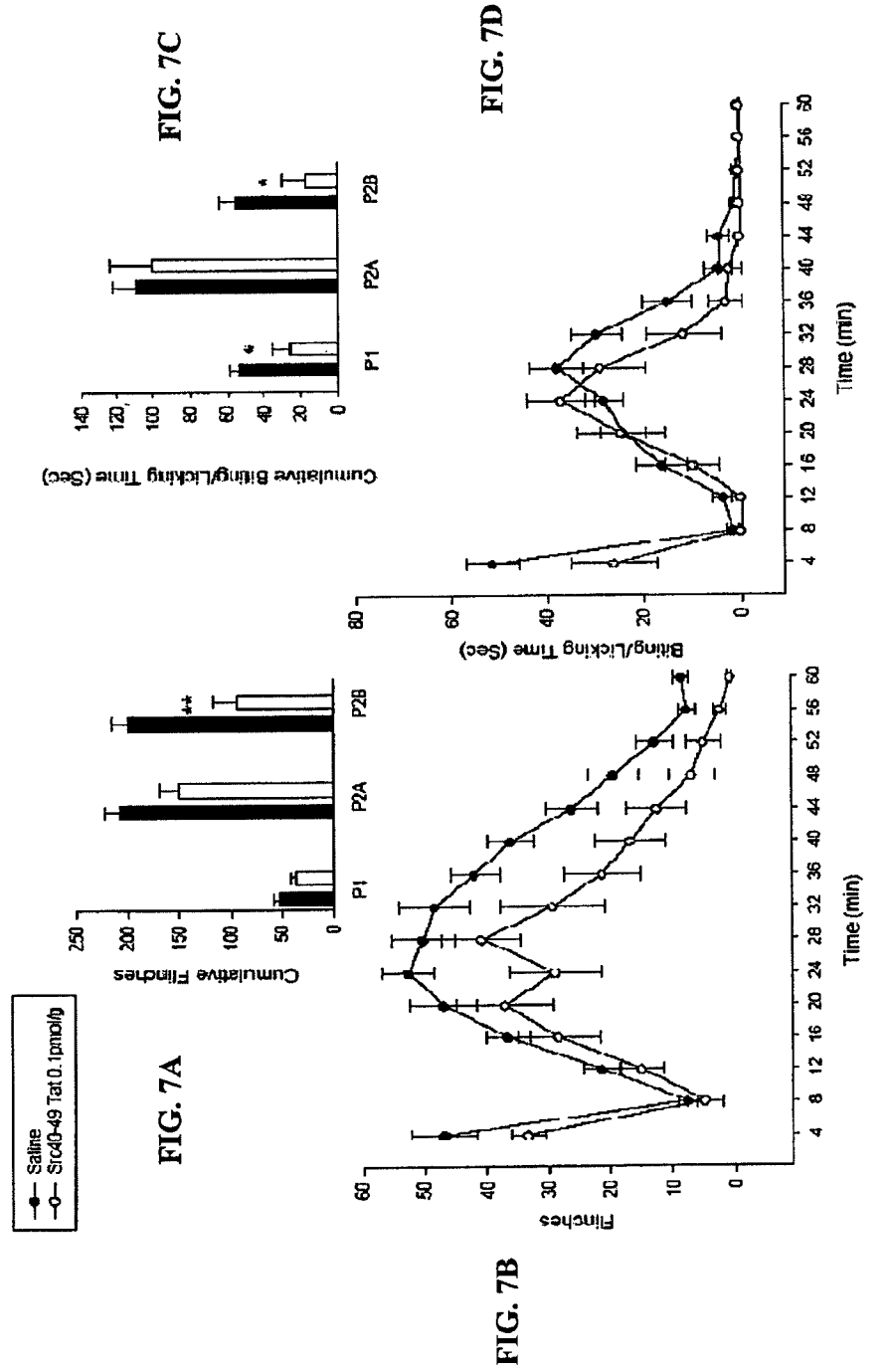
FIGS. 7A-D show results of experiments showing the effects of TSUDAPI-1 on 2.5% formalin induced flinching or biting/licking behaviors.

FIGS. 7A-D show the effect of Src40-49Tat (0.1 pmol) on 2.5% formalin induced flinching or biting/licking behaviors. Peptides or saline controls were injected 45 minutes before behavioral testing. FIG. 7B shows measurement of flinching behaviors observed within an hour. FIG. 7A shows the cumulative flinches in different phases observed within the hour. P1 represents a time period of 0-8 minutes; P2A represents a time period of 12-28 minutes and P2B represents a time period of 32-60 minutes. Values depict means (n=7, Src40-49Tat; n=20, saline). $P<0.05$, $P<0.01$ with student t test compared to saline control. FIG. 7D shows measurement of the time of each biting/licking behavior observed within an hour. FIG. 7C shows the cumulative biting/licking behaviors in different phases observed within the hour. P1 represents a time period of 0-8 minutes; P2A represents a time period of 12-28 minutes and P2B represents a time period of 32-60 minutes. Values depict means (n=7, Src40-49Tat; n=20, saline). $P<0.05$, $P<0.01$ with student t test compared to saline control.

FIGS. 8A-D show the effect of HIV-Tat (1 pmol/g) on 2.5% formalin induced flinching or biting/licking behaviors. Peptides or saline controls were injected 45 minutes before behavioral testing. FIG. 8B shows measurement of flinching behaviors observed within an hour. FIG. 8A shows the cumulative flinches in different phases observed within the hour. P1 represents a time period of 0-8 minutes; P2A represents a time period of 12-28 minutes and P2B represents a time period of 32-60 minutes. Values depict means (n=7, HIV-Tat; n=20, saline). $P<0.05$, $P<0.01$ with student t test compared to saline control. FIG. 8D shows measurement of the time of each biting/licking behavior observed within an hour. FIG. 8C shows the cumulative biting/licking behaviors in different phases observed within the hour. P1 represents a time period of 0-8 minutes; P2A represents a time period of 12-28 minutes and P2B represents a time period of 32-60 minutes. Values depict means (n=7, HIV-Tat; n=20, saline). $P<0.05$, $P<0.01$ with student t test compared to saline control. As compared to HIV-Tat alone and the saline control, the Src40-49Tat peptide is shown to reduce pain behaviors over a time period of an hour.

It is known that tyrosine phosphorylation of the NR2 subunits plays a key role in NMDA receptor activation (Moon et al. PNAS USA 91:3954-3958 1994; Lau et al. Journal of Biological Chemistry 270:20036-20041 1995; Xiong et al. Journal of Neuroscience 19:RC37(1-6) 1999). It is also known that inflammatory hyperalgesia is associated with rapid and prolonged enhancement of tyrosine phosphorylation of the NR2B subunits of NMDA receptors (Guo et al. The Journal of Neuroscience 22(14):6208-6217 2002). Thus, considering that protein phosphorylation is a major mechanism for both normal and pathological receptor function, the effect of the formalin test on receptor phosphorylation was examined.

FIGS. 14A-D illustrate the increase in tyrosine phosphorylation of the NR2B subunit after formalin injection (FIGS. 14A-B) and further illustrate that this increase of NR2B tyrosine phosphorylation is significantly reduced by intrathecal (i.t.) administration of Src40-49Tat (SEQ ID NO:2) (FIGS. 14C-D). FIG. 14A shows a western blot of an immunoprecipitation using an anti-NR2B antibody and an anti-phosphorylated tyrosine antibody. It can be seen that by 60 minutes post-injection of formalin, tyrosine phosphorylation of the NR2B subunit increases. FIG. 14B shows a graph quantifying the tyrosine phosphorylation calculated as a percent of the control. This data was calculated prior to formalin injection and at three times post-injection; at 5 minutes, 30 minutes and 60 minutes. As can be seen, the amount of NR2B subunit that is phosphorylated peaks at around 30 minutes post-injection. FIG. 14C shows another western blot of an immunoprecipitation using an anti-NR2B antibody and an anti-phosphorylated tyrosine antibody. This blot evidences the reduction of formalin-induced tyrosine phosphorylation resulting from treatment with Src40-49Tat (SEQ ID NO:2) and the absence of reduction resulting from treatment with scrambled Src40-49Tat (sSrc40-49Tat). FIG. 14D shows a graph quantifying the tyrosine phosphorylation (after treatment with Src40-49Tat or sSrc40-49) calculated as a percent of the control. This data was calculated at 60 minutes post-injection of formalin to treated animals.

EXAMPLE 8

ND2-Src interaction in multiple tissues

Total soluble protein was prepared from pre-weighed rat tissues by homogenization at 4° C. in 0.25 M sucrose/10 mM HEPES-NaOH, 1 mM EDTA, pH 7.4 with 2 µg/ml each of aprotinin, pepstatin A, and leupeptin. Following brief configuration of the samples at 4 000 g, NP-40 was added to 1% (vol/vol) to the cleared supernatants. After incubation for 10 minutes, the protein concentration of the samples was determined by detergent compatible protein assay (BioRad Laboratories, Mississauga, Ontario) and equilibrated. The solubilized proteins were centrifuged briefly at 14 000 g to remove insoluble material and then incubated with 5 µg of either anti-ND2 (rabbit polyclonal from Dr. R.F. Doolittle, UCSD, CA; described in Mariottini et al. PNAS USA 83:1563-1567 1986), anti-Src (mouse monoclonal clone 327 from J. Bolen, DNAX, Palo Alto, Calif.) or control, non-specific rabbit or mouse IgG (Sigma) overnight at 4° C. Immune complexes were isolated by the addition of 10 µl of protein G-SEPHAROSE beads followed by incubation for 2 hours at 4° C. Immunoprecipitates were then washed three times with RIPA buffer, re-suspended in RIPA buffer+SDS-PAGE sample buffer and boiled for 5 minutes. The samples were resolved by SDS-PAGE, transferred to nitrocellulose membranes and analyzed by immunoblotting with anti-ND2, anti-Src or anti-Fyn (mouse monoclonal clone 25, Pharmingen, Mississauga, Ontario). Bound antibody was then detected on film using appropriate secondary antibody/HRP conjugates and an ECL kit (Amersham Pharmacia Biotech). For control immunoprecipitations under denaturing conditions, SDS was added to the initial protein samples to a final concentration of 0.4% and the samples were boiled for 5 minutes and rapidly cooled to 4° C. prior to the addition of the antibodies used for immunoprecipitation. In addition, pre-adsorption of the anti-ND2 antibody with antigenic peptide prevented antibody signal detection on immunoblots.

Figure 10:
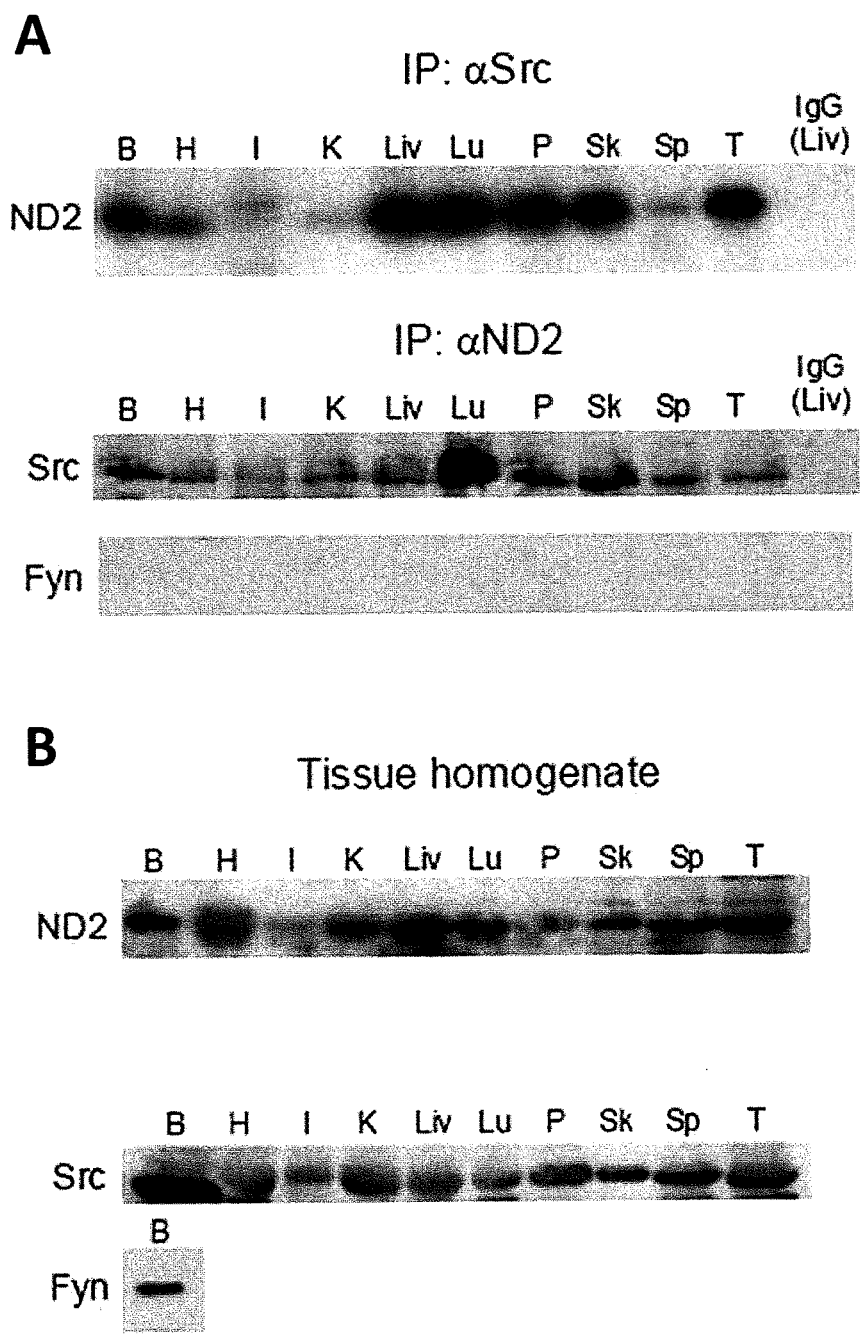
FIGS. 10A-B show immunoblots evidencing that ND2 and Src interact in multiple, diverse tissues.

Non-receptor tyrosine kinase Src and ND2 are both expressed in cells of multiple, diverse tissues. Illustrative, albeit non-limiting, examples are peripheral nervous system tissue, central nervous system tissue, heart, intestine, kidney, liver, lung, pancreas, skeletal muscle, spleen, testis, bone, skin and brain. The data presented in FIGS. 10A-B shows that ND2 and Src interact in multiple, diverse tissues. Immunoblots of co-immunoprecipitates from various tissues (FIG. 10A) and tissue homogenates (FIG. 10B) probed with anti-ND2, anti-Src, or anti-Fyn as indicated. Tissues: B—brain; H—heart; I—intestine; K—kidney; Liv—liver; Lu—lung; P—pancreas; Sk—skeletal muscle; Sp—spleen and T—testis. Non-specific IgG applied to liver homogenate was used as a negative control for co-immunoprecipitation. Immunoblotting of Fyn protein from brain was used as a positive control for the anti-Fyn antibody. In these experiments the cell lysates were prepared using non-denaturing conditions, but when denaturing conditions were used to prepare the proteins, no co-immunoprecipitation of Src by anti-ND2 or of anti-Src was found (data not illustrated).

EXAMPLE 9

Src40-49Tat (TSUDAPI-1) inhibits neuropathic pain

Increased activity of NMDA receptors is known to play a major role in pain produced by peripheral nerve injury (Ren et al. Journal of Orofacial Pain 13:155-163 1999). This type of pain is debilitating and treatments remain relatively ineffective. Antagonists of the NMDA receptor complex have been suggested as potential drugs for neuropathic pain management (Planells-Cases et al. Mini Review of Medicinal Chemistry 3(7):749-756 2003). However, non-selective blocking of NMDA receptor function is deleterious, since complete blockade of synaptic transmission mediated by NMDA receptors is known to hinder neuronal survival (Ikonomidou et al. Lancet: Neurology 1:383-386 2002; Fix et al. Experimental Neurology 123:204 1993; Davis et al. Stroke 31:347 2000; Morris et al. Journal of Neurosurgery 91:737 1999). The method of the instant invention selectively blocks NMDAR-mediated excitatory post-synaptic current (EPSC) without effecting the AMPA (GluR1-containing α-amino-3-hydroxy-5-methyl-4-isoxazolepropionic acid) component.

Pain induced by cuff implantation, in a laboratory animal such as a rat or mouse, is an art-accepted model of neuropathic pain. Generally, in cuff implantation a nerve root in the sciatic nerve leading to a hind paw is tied off by surgical implantation of a "cuff", for example, a polyethylene ring. Over a period of time the nerve degenerates and a neuropathic pain pattern develops. A control is created by subjecting another group of animals to "sham surgery", a procedure wherein the animals receive the same type of surgery as cuff implantation without the physical implantation of the cuff. After a period of time, the paw is stimulated by a series of filaments or exposure to a small amount of moderate heat. Pain is measured by observation of "paw withdrawal", in general, if the animal lifts the paw and the time it takes to do so. Typically, an animal not experiencing neuropathic pain will not respond to the stimuli. When testing using filaments, threshold is defined in terms of force. A reduction in threshold suggests the development of allodynia. This testing method is described in the art; Ren Physiological Behavior 67:711-716 1999 and Guo et al. The Journal of Neuroscience 22(14): 6208-6217 2002.

Figure 11:
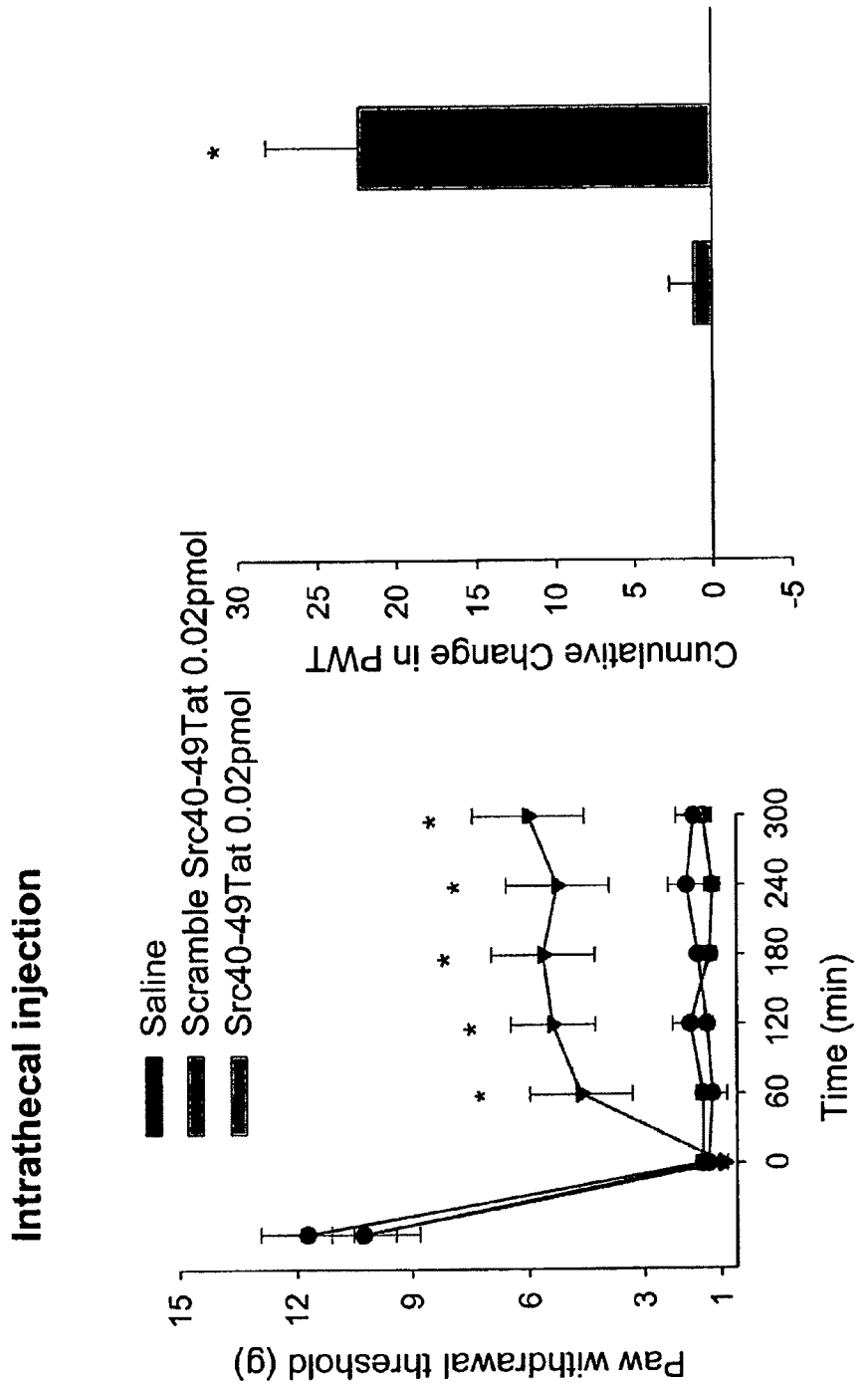
FIG. 11 shows graphs evidencing that intrathecal injection of 0.02 pmol of Src40-49TAT (TSUDAPI-1, SEQ ID NO:2) significantly reverses allodynia in rats.

In this experiment, tactile allodynia was induced in a group of mice by cuff implantation and symptoms were observed as early as day 3 post-surgery. Allodynia was allowed to fully develop at 8-10 days post-surgery before the "paw withdrawal" tests were performed. A group of mice received an intrathecal (introduced into the space under the arachnoid membrane of the brain or spinal cord) injection of 0.02 pmol of Src40-49Tat (TSUDAPI-1, SEQ ID NO:2), a second group of mice received an intrathecal injection of 0.02 pmol Scramble Src40-49Tat and a third group of mice received an intrathecal injection of saline. "Scramble Src40-49Tat" refers to TSUDAI-1 (SEQ ID NO:2) having a "scrambled" sequence, i.e. having amino acid residues out of order from the normal. The results are presented in FIG. 11. Green represents Src40-49Tat (TSUDAPI-1, SEQ ID NO:2), grey represents Scramble Src40-49Tat and red represents saline. Src40-49Tat (TSUDAPI-1, SEQ ID NO:2), but not Scramble Src40-49Tat or saline, significantly reversed allodynia. The reversal effect was observed as early as one hour following administration. The reversal was significant at more than 5 hours post injection, with PWT 6.03±1.45 g (Src40-49Tat) versus 1.7±0.47 g (scrambled Src40-49Tat) ($p<0.05$).

Figure 12:
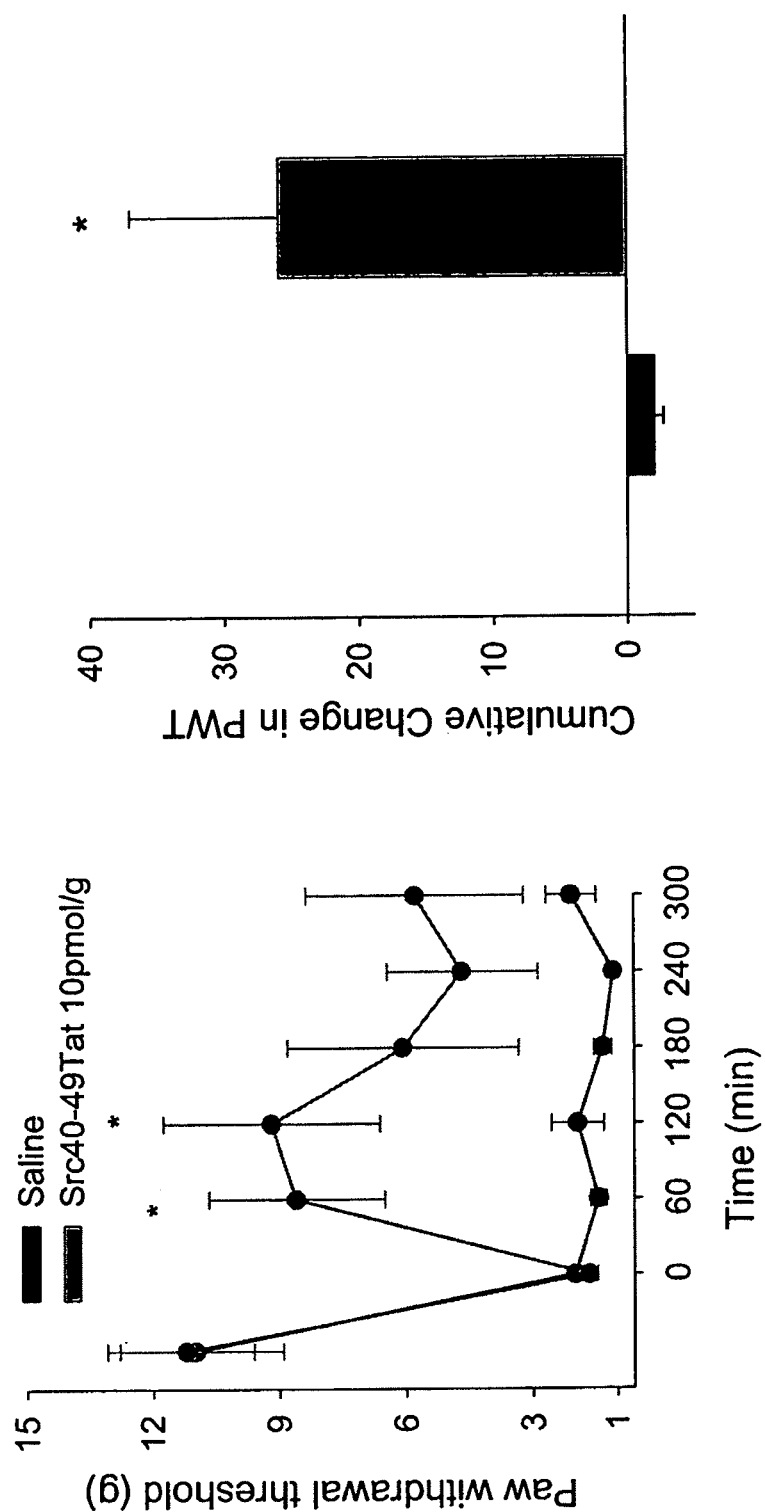
FIG. 12 shows graphs evidencing that intravenous injection of 10 pmol/g of Src40-49TAT (TSUDAPI-1, SEQ ID NO:2) significantly reverses allodynia in rats.

Another group of mice received an intravenous injection of 10 pmol/g of Src40-49Tat (TSUDAPI-1, SEQ ID NO:2) and a second group of mice received an intravenous injection of saline. The results are presented in FIG. 12. Green represents Src40-49Tat (TSUDAPI-1, SEQ ID NO:2) and red represents saline. Src40-49Tat (TSUDAPI-1, SEQ ID NO:2), but not saline, significantly reversed allodynia. The reversal effect was observed as early as one hour following administration. The anti-allodynic effect of the peptide (SEQ ID NO:2) peaked at 2 hours following injection, with PWT 9.28±2.55 g (Src40-49Tat) versus 1.95±0.617 g (saline) ($p<0.05$).

Protein phosphorylation is a major mechanism for receptor function. It is known that tyrosine phosphorylation of the NR2 subunits plays a key role in NMDA receptor activation (Moon et al. PNAS USA 91:3954-3958 1994; Lau et al. Journal of Biological Chemistry 270:20036-20041 1995; Xiong et al. Journal of Neuroscience 19:RC37(1-6) 1999). It is also known that inflammatory hyperalgesia is associated with rapid and prolonged enhancement of tyrosine phosphorylation of the NR2B subunits of NMDA receptors (Guo et al. The Journal of Neuroscience 22(14):6208-6217 2002).

In this experiment, a significant increase of tyrosine phosphorylation of NMDA receptor NR2B subunits in spinal cord dorsal horn tissue was observed in cuffed rats but not in sham-operated rats (FIG. 15A). Intrathecal injection of 0.02 pmol Src40-49Tat (TSUDAPI-1, SEQ ID NO:2) significantly reversed the increase in tyrosine phosphorylation (FIG. 15B). FIG. 15A shows a western blot of an immunoprecipitation using an anti-NR2B antibody and anti-phosphorylated tyrosine antibody. FIG. 15B shows a graph quantifying the tyrosine phosphorylation calculated as a percent of the control. This graph represents quantification of band (from western blots) density in three experiments.

Figure 13:
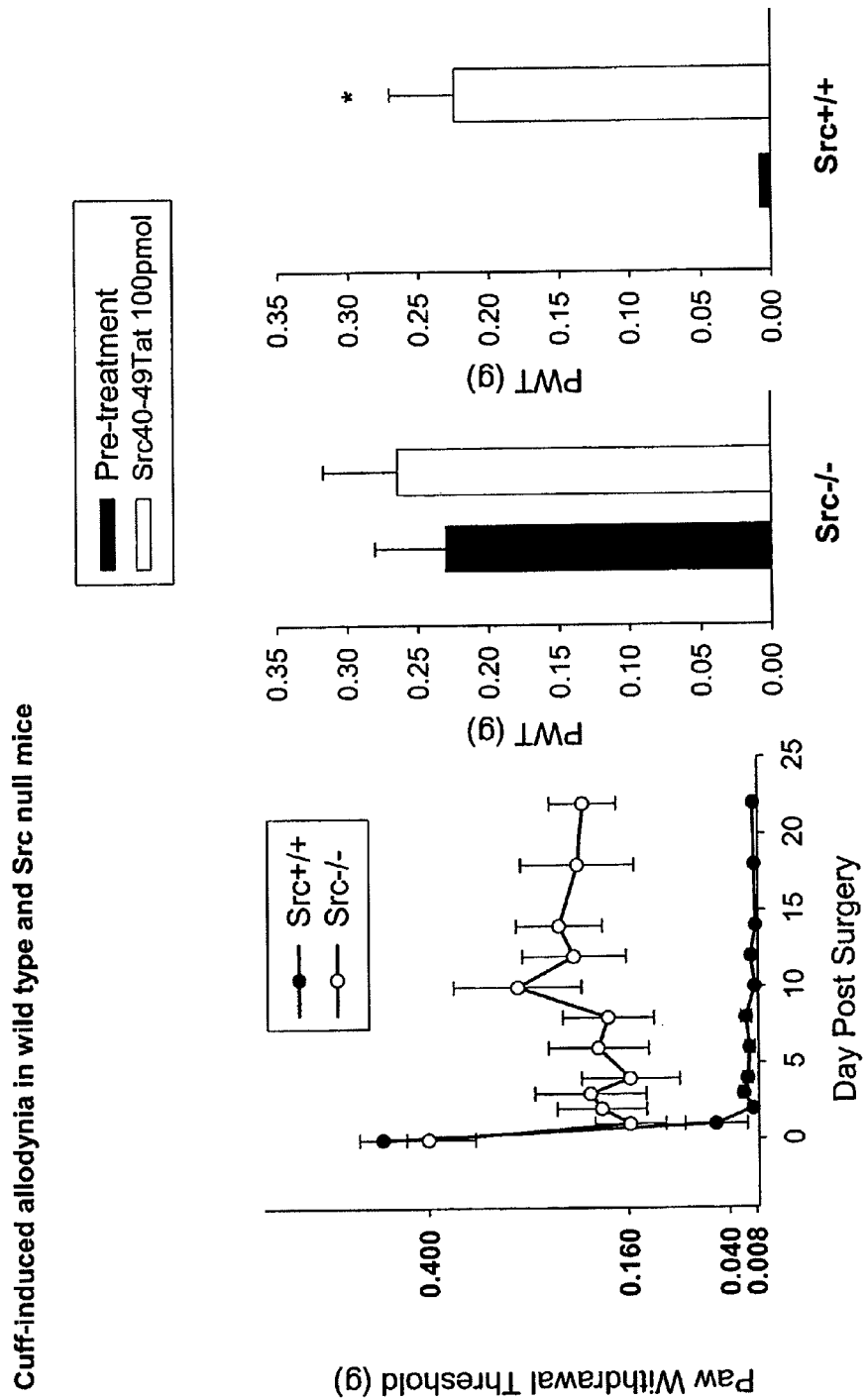
FIG. 13 shows graphs evidencing that intravenous injection of 100 pmol Src40-49TAT (TSUDAPI-1, SEQ ID NO:2) significantly reverses allodynia in wild type mice but does not further increase paw withdrawal threshold (PWT) in Src null mice.

Another experiment was performed to compare cuff-induced allodynia in wild-type mice to Src kinase null mice (Src kinase knock-out mice). The results are shown in FIG. 13. The PWT was tested in the mice prior to surgery. The basal PWT in Src kinase null mice was not different from that of wild-type mice; see black bars in graphs in center and right hand side in FIG. 13, Src −/− and Src +/+. Both groups of mice received an intravenous injection of 100 pmol of Src40-49Tat (TSUDAPI-1, SEQ ID NO:2). Allodynia was depressed in Src kinase null mice throughout the testing time course, with PWT 0.01±1.53 g (wild) versus 0.21±0.04 g (null) (p<0.05) at 22 days post surgery (left graph in FIG. 13). Treatment with Src40-49Tat (100 pmol, intravenous injection) significantly reversed allodynia in wild-type mice from 0.008±0.0 g to 0.23±0.05 g (p<0.05), but did not further increase PWT in null mice. Nerve-injury induced increase in phosphorylation of the NR2B subunit was found to be depressed in both wild-type and Src kinase null mice. Treatment with Src40-49Tat did not further decrease phosphorylation of NR2B subunits in Src kinase null mice.

Thus, the instant inventors concluded that loss of Src or depressed action of Src through treatment with Src40-49Tat (TSUDAPI-1, SEQ ID NO:2) inhibits Src-mediated NMDAR up-regulation dependent neuropathic pain.

In Summary

The main criteria for identifying ND2 as the protein mediating the interaction between NMDARs and the unique domain of Src, as inferred from previous work (Ali et al. Current Opinion in Neurobiology 11:336-342 2001; Yu et al. Science 275:674-678 1997) are as follows: ND2 must bind directly to the unique domain of Src through amino acids 40-58(specifically 40-49; SEQ ID NO:1); this binding must be prevented by the Src40-58 (specifically 40-49) peptide; ND2 must be present at excitatory synapses and must be a component of the NMDAR complex; and lack of ND2 must prevent the upregulation of NMDAR activity by endogenous Src.

ND2 was first considered as a potential Src unique domain-binding protein when overlapping clones of ND2 in two separate yeast two-hybrid experiments were isolated. Subsequently, the direct interaction of the Src unique domain and ND2 was confirmed through in vitro binding assays using recombinant proteins. Through these experiments the ND2.1 region was identified as necessary and sufficient for interacting with the Src unique domain. ND2.1 bound directly to the Src40-58 (specifically 40-49) peptide and the in vitro binding of the Src unique domain to ND2.1 was prevented by Src40-58 (specifically 40-49). Src and ND2 co-immunoprecipitated with each other in brain homogenates and PSD protein preparations. The co-immunoprecipitation was prevented by Src40-58(specifically 40-49), implying that the Src-ND2 interaction identified in vitro may occur in vivo. In addition to finding ND2 in PSD protein preparations, ND2-immunoreactivity was found by immunogold electron microscopy in PSDs in the CA1 hippocampus. Moreover, co-immunoprecipitation experiments indicated that ND2 is a component of the NMDAR complex and that the Src-ND2 interaction is required for the association of Src, but not ND2, with NMDARs. It was found that depleting ND2 suppresses Src association with the NMDAR complex and prevents the upregulation of NMDAR function by activating endogenous Src at excitatory synapses. Src40-49 (SUDAPI-1; SEQ ID NO:1) was identified as the specific peptide that interacts with ND2 as Src50-58 alone did not interact with ND2. Finally, it was found that TAT-Src40-49 (TSUDAPI-1; SEQ ID NO:2) as administered to rats reduced pain behavior in the formalin test. These multiple, converging lines of evidence lead to the conclusion that ND2 is the protein mediating the interaction between NMDARs and the unique domain of Src.

ND2 is mitochondrially encoded and translated, and yet it is found within the PSDs of glutamatergic synapses in the brain. The other mitochondrial proteins examined, ND4 and Cyto 1, were not detected in the PSD fraction implying that this fraction is not contaminated non-specifically by mitochondrial proteins. Further, ND2-immunoreactivity by immunogold electron microscopy was found within structurally-identified PSDs in dendritic spines of CA1 neurons. In this preparation, proteins are immobilized by tissue fixation precluding the possibility that ND2 could have relocated from the mitochondria to the PSD during processing. Moreover, because dendritic spines are devoid of mitochondria (Shepherd et al. Journal of Neuroscience 18(20):8300-8310 1998) the ND2 immunoreactivity cannot be accounted for by mitochondria abutting the PSD. Taken together these findings indicate that ND2, but not the entire Complex I, is normally present within the PSD. The PSD contains many enzymes that may be involved in regulating synaptic functioning (P. Siekevitz Proceedings of the National Academy of Science USA 82:3494-3498 1985) including glycolytic enzymes capable of generating ATP (Wu et al. Proceedings of the National Academy of Science USA 94:13273-13278 1997). However, without other components of Complex I it is unlikely that ND2 functions catalytically within the PSD.

Thus, in addition to its localization in mitochondria and function as a component of Complex I, the present results indicate that ND2 has a second location and function in outside the mitochondria. Mitochondria are intimately linked to overall cellular functioning through generation of ATP by oxidative phosphorylation. Mitochondria are also known to be key for sequestration of intracellular calcium (D. D. Friel Cell Calcium 28:307-316 2000; R. Rizzuto Current Opinion in Neurobiology 11:306-311) and to participate in programmed cell death (Gorman et al. Developmental Neuroscience 22:348-358 2000; M. P. Mattson National Review of Molecular and Cellualr Biology 1:120-129 2000). Some mitochondrial proteins are known to be present at extra-mitochondrial sites (Soltys et al. Trends in Biochemical Science 24:174-177 1999; Soltys et al. International Review of Cytology 194:133-196 1999). But, the experiments described herein indicate a new type of function for a mitochondrial protein outside this organelle, that is ND2 acts as an adapter protein that anchors Src within the NMDAR complex, where it thereby allows Src to upregulate NMDAR activity.

Upregulating the activity of NMDARs is a major function of Src in neurons in the adult CNS (Lu et al. Science 279: 1363-1368 1998; Pelkey et al. Neuron 34:127-138 2002; Huang et al. Neuron 29:485-496 2001) and this mediates the induction of long-term potentiation (LTP) of excitatory synaptic transmission in CA1 neurons in the hippocampus (Ali et al. Current Opinion in Neurobiology 11:336-342 2001). The findings described herein imply that the ND2-Src interaction is essential for LTP induction as LTP in CA1 neurons is prevented by Src40-58 and by anti-Src1, an antibody that recognizes this amino acid sequence within the Src unique domain and which prevents the Src unique domain interaction with ND2.1 in vitro (J.R.G., M.W.S. unpublished observations). LTP at Schaffer collateral-CA1 synapses is the prototypic example of NMDAR-dependent enhancement of excitatory synaptic transmission, which is observed at numerous types of glutamatergic synapses throughout the CNS (Malenka et al. Science 285:1870-1874 1999). In addition, Src has been implicated in NMDAR-dependent seizures (Sanna et al. Proceedings of the National Academy of Science 97:8653-8657 2000), chronic pain (Guo et al. Journal of Neuroscience 22:6208-6217 2002) and neurotoxicity (Pei et al. Journal of Cerebral Blood Flow Metabolism 21:955-963 2001). Thus, the discovery of the Src-ND2 interaction at NMDARs, which is disclosed herein, defines a protein-protein interaction of general relevance to regulation of neuronal function, synaptic plasticity, and pathophysiology in the CNS.

Additionally, by showing an extramitochondrial action for a protein encoded in the mitochondrial genome a previously unsuspected means by which mitochondria regulate cellular function has been identified. Because ND2 and Src are broadly expressed, the interaction of ND2 with the Src unique domain may be of general relevance for control of Src signaling (Example 8 and FIGS. 10A-B).

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for ameliorating pain in a subject by modifying N-methyl-D-aspartate receptor (NMDAR) interaction with non-receptor tyrosine kinase Src in cells of said subject comprising the steps of:
   (a) providing a composition including a Src-binding portion of the ND2.1 peptide of SEQ ID NO: 7 and a carrier effective to transport the Src-binding portion into cells; and
   (b) administering the composition of step (a) to said subject in an amount effective to achieve modification of said NMDAR interaction with said non-receptor tyrosine kinase Src in said cells wherein said modification ameliorates pain in said subject.

2. The method as in claim 1 wherein said carrier is selected from the group consisting of HIV Tat domain peptides, arginine-rich peptides, antennapedia peptides, VP22 herpes simplex viral peptides and lipids.

3. The method as in claim 1 wherein said pain is inflammatory pain.

4. The method as in claim 1 wherein said pain is neuropathic pain.

* * * * *